US011267871B2

(12) United States Patent
Arndt et al.

(10) Patent No.: US 11,267,871 B2
(45) Date of Patent: Mar. 8, 2022

(54) TOPICAL APPLICATION FOR AN ANTI-HSV ANTIBODY

(71) Applicant: Heidelberg ImmunoTherapeutics GmbH, Heidelberg (DE)

(72) Inventors: Michaela Arndt, Mannheim (DE); Jürgen Krauss, Mannheim (DE); Dirk Jäger, Heidelberg (DE)

(73) Assignee: Heiselberg ImmunoTherapeutics GmbH, Heidelberg (DE)

( * ) Notice: Subject to any disclaimer, the term of this patent is extended or adjusted under 35 U.S.C. 154(b) by 0 days.

(21) Appl. No.: 15/320,501

(22) PCT Filed: Jun. 25, 2015

(86) PCT No.: PCT/EP2015/064378
§ 371 (c)(1),
(2) Date: Dec. 20, 2016

(87) PCT Pub. No.: WO2015/197763
PCT Pub. Date: Dec. 30, 2015

(65) Prior Publication Data
US 2017/0152304 A1    Jun. 1, 2017

(30) Foreign Application Priority Data

Jun. 26, 2014   (EP) .................... 14174174

(51) Int. Cl.
| C07K 16/00 | (2006.01) |
| A61K 39/245 | (2006.01) |
| A61K 45/06 | (2006.01) |
| C07K 16/08 | (2006.01) |
| A61K 39/42 | (2006.01) |
| A61K 39/00 | (2006.01) |

(52) U.S. Cl.
CPC ............ *C07K 16/087* (2013.01); *A61K 39/42* (2013.01); *A61K 45/06* (2013.01); *A61K 2039/505* (2013.01); *A61K 2039/54* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 6,156,313 A | * | 12/2000 | Burton ................ | C07K 16/087 424/142.1 |
| 9,657,088 B2 | | 5/2017 | Roggendorf et al. | |
| 2007/0274997 A1 | | 11/2007 | Simmons et al. | |
| 2011/0033389 A1 | * | 2/2011 | Chen .................... | C07K 16/087 424/9.6 |
| 2014/0302062 A1 | * | 10/2014 | Haynes ................ | C07K 16/087 424/159.1 |

FOREIGN PATENT DOCUMENTS

| EP | 2308895 A1 | | 4/2011 |
| WO | 2005023303 A1 | | 3/2005 |
| WO | WO 2005/023303 | * | 3/2005 |
| WO | 2010128053 A1 | | 11/2010 |
| WO | 2010129033 A2 | | 11/2010 |
| WO | 2011038933 A2 | | 4/2011 |

OTHER PUBLICATIONS

Krawczyk et al. Overcoming drug-resistant herpes simplex virus (HSV) infection by a humanized antibody. PNAS, 110(17): 6760-6765, Apr. 23, 2013.*
Moser et al. Correlation of Herpes Simplex Virus Antibody Titers and Specific Lymphocyte Stimulation in Adult Blood Donors. Journal of Clinical Microbiology, Jan. 1981, 13: 36-41.*
Cocchi et al. Cell-to-Cell Spread of Wild-Type Herpes Simplex Virus Type 1, but Not of Syncytial Strains, Is Mediated by the Immunoglobulin-Like Receptors That Mediate Virion Entry, Nectin1 (PRR1/HveC/HIgR) and Nectin2 (PRR2/HveB). J. Virol. 2000, 74:3909-3917.*
De Logu et al. Characterization of a Type-Common Human Recombinant Monoclonal Antibody to Herpes Simplex Virus with High Therapeutic Potential. J. Clin. Microbiol. 1998, 36: 3198-3204.*
Wald et al. Chapter 36 Persistence in the population: epidemiology, transmission. In Arvin et al., editors. Human Herpesviruses: Biology, Therapy, and Immunoprophylaxis. Cambridge: Cambridge University Press; 2007.*
Emmert et al. Treatment of Common Cutaneous Herpes Simplex Virus Infections. Am Fam Physician. Mar. 15, 2000;61 (6):1697-1704.*
International Preliminary Report on Patentability and Written Opinion for PCT/EP2015/064378 dated Jan. 5, 2017.
Extended European Search Report from corresponding EP 14 17 4174, dated Jan. 16, 2015.
Krawczyk et al., "Overcoming Drug-Resistant Herpes Simplex Virus (HSV) Infection by a Humanized Antibody", Proceedings of the National Academy of Sciences, vol. 110, No. 17, Apr. 8, 2013, XP055160621.

(Continued)

*Primary Examiner* — Nianxiang Zou
(74) *Attorney, Agent, or Firm* — Michele M. Wales; InHouse Patent Counsel, LLC

(57) ABSTRACT

Described is an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered as well as to a pharmaceutical composition comprising an effective amount of said antibody or antigen-binding fragment thereof and at least one pharmaceutically acceptable excipient.

Figure 1:
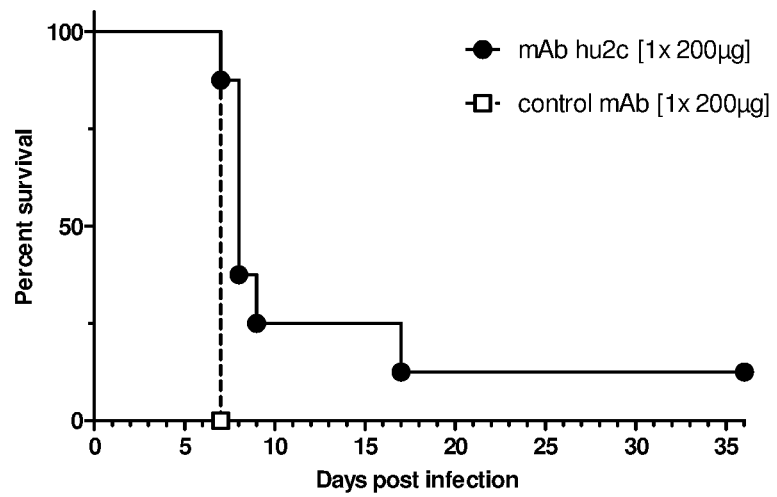
Figure 1:
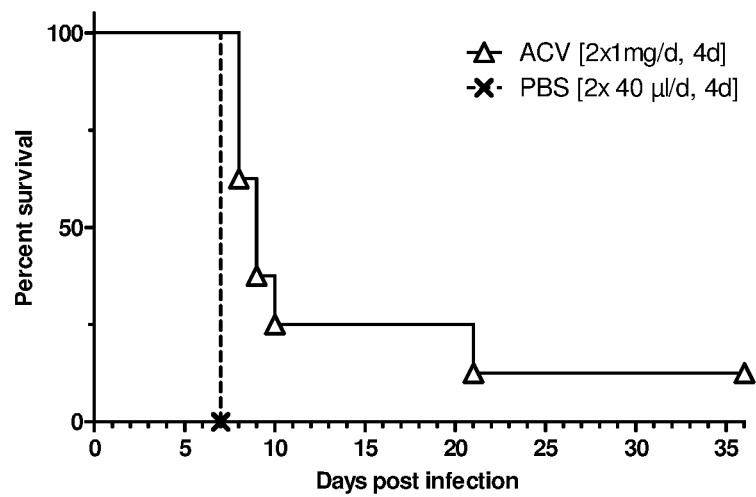

19 Claims, 2 Drawing Sheets
Specification includes a Sequence Listing.

(56) References Cited

OTHER PUBLICATIONS

Daumer et al., "Characterisation of the Epitope for a Herpes Simplex Virus Glycoprotein B-specific Monoclonal Antibody with High Protective Capacity", Medical Microbiology and Immunology, vol. 200, No. 2, Oct. 8, 2010, pp. 85-97, XP055160623.

International Search Report & Written Opinion from corresponding PCT/EP2015/064378, dated Sep. 17, 2015.

European Office Action dated Jan. 2, 2018 and received in 15733409. 5.

Sherwood, et al., "Controlled Release of Antibodies For Long-Term Topic Passive Immunoprotection Of Female Mice Against Genital Herpes", Nature Biotechnology, vol. 14, Apr. 14, 1996, pp. 468-471 (XP055436671).

Office of Action dated Jul. 23, 2018 received in corresponding Russian Patent Application No. 2017 102 387 and translation.

Japanese Office action and translation dated Jan. 24, 2019 and received for corresponding JP Patent Application No. 2016-575171.

Baumgarth et al., "B-1 and B-2 Cell-derived Immunoglobulin M Antibodies Are Nonredundant Components of the Protective Response to Influenza Virus Infection", J. Exp. Med., vol. 192, No. 2, pp. 271-280, (2000).

Briles et al., "Antiphosphocholine Antibodies Found in Normal Mouse Serum are Protective Against Intravenousinfection With Type 3 *Streptococcus pneumoniae*", J. Exp. Med., vol. 153, pp. 694-705, (1981).

Desphande et al., "Dual Role of B Cells in Mediating Innate and Acquired Immunity to Herpes Simplex Virus Infections", Cellular Immunology, vol. 202, pp. 79-87, (2000).

Gobet et al., "The Role of Antibodies in Natural and Acquired Resistance of Mice to Vesicular Stomatitis Virus", Expl Cell Biol, vol. 56, pp. 175-180, (1988).

Haury et al., "The Repertoire of Serum IgM in Normal Mice is Largely Independent of External Antigenic Contact", Eur.J. Immunol., vol. 27, pp. 1557-1563, (1997).

Ochsenbein et al., "Control of Early Viral and Bacterial Distribution and Disease by Natural Antibodies", Science, vol. 286, pp. 2156-2159, (1999).

\* cited by examiner

SEQUENCE LISTING

```
<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: 2cVH CDR1

<400> SEQUENCE: 1

Thr Ser Gly Met Ser Val Gly
1               5

<210> SEQ ID NO 2
<211> LENGTH: 16
<212> TYPE: PRT
<213> ORGANISM: Artificial Sequence
<220> FEATURE:
<223> OTHER INFORMATION: 2cVH CDR2

<400> SEQUENCE: 2

His Ile Trp Trp Asn Asn Asp Lys Tyr Tyr Lys Pro Ala Leu Lys Ser
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: 2cVH CDR3

<400> SEQUENCE: 3

Ile Tyr Tyr Gly Tyr Arg Pro Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: 2cVL CDR1

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: 2cVL CDR2

<400> SEQUENCE: 5

Lys Val Ser Asn Arg Phe Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: 2cVL CDR3

<400> SEQUENCE: 6

```
Phe Gln Gly Ser His Val Pro Trp Ser
1               5
```

<210> SEQ ID NO 7
<211> LENGTH: 122
<212> TYPE: PRT
<213> ORGANISM: Artificial Sequence
<220> FEATURE:
<223> OTHER INFORMATION: human germline VH framework
<220> FEATURE:
<221> NAME/KEY: VARIANT
<222> LOCATION: (100)..(107)
<223> OTHER INFORMATION: Xaa can be any naturally occurring amino acid

<400> SEQUENCE: 7

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Tyr Phe Asp Tyr Trp
            100                 105                 110

Gly Gln Gly Thr Leu Val Thr Val Ser Ser
        115                 120
```

<210> SEQ ID NO 8
<211> LENGTH: 114
<212> TYPE: PRT
<213> ORGANISM: Artificial Sequence
<220> FEATURE:
<223> OTHER INFORMATION: human germline VL framework

<400> SEQUENCE: 8

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Glu Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95
```

Arg Ile Glu Phe Pro Trp Thr Phe Gly Gln Gly Thr Lys Val Glu Ile
                100                 105                 110

Lys Arg

<210> SEQ ID NO 9
<211> LENGTH: 122
<212> TYPE: PRT
<213> ORGANISM: Artificial Sequence
<220> FEATURE:
<223> OTHER INFORMATION: VH of the humanized mAb hu2c antibody

<400> SEQUENCE: 9

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala His Ile Trp Trp Asn Asn Asp Lys Tyr Tyr Lys Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Tyr Gly Tyr Arg Pro Tyr Ala Met Asp Tyr Trp
            100                 105                 110

Gly Gln Gly Thr Leu Val Thr Val Ser Ser
        115                 120

<210> SEQ ID NO 10
<211> LENGTH: 113
<212> TYPE: PRT
<213> ORGANISM: Artificial Sequence
<220> FEATURE:
<223> OTHER INFORMATION: VL of the humanized mAb hu2c antibody

<400> SEQUENCE: 10

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Ser Phe Gly Gln Gly Thr Lys Val Glu Ile Lys
            100                 105                 110

Arg

<210> SEQ ID NO 11
<211> LENGTH: 903
<212> TYPE: PRT
<213> ORGANISM: HSV1 strain F

```
<400> SEQUENCE: 11

Met Arg Gln Gly Ala Ala Arg Gly Cys Arg Trp Phe Val Val Trp Ala
1               5                   10                  15

Leu Leu Gly Leu Thr Leu Gly Val Leu Val Ala Ser Ala Ala Pro Ser
            20                  25                  30

Ser Pro Gly Thr Pro Gly Val Ala Ala Thr Gln Ala Ala Asn Gly
        35                  40                  45

Gly Pro Ala Thr Pro Ala Pro Pro Ala Pro Gly Pro Ala Pro Thr Gly
50                  55                  60

Asp Thr Lys Pro Lys Lys Asn Lys Lys Pro Lys Asn Pro Pro Pro
65                  70                  75                  80

Arg Pro Ala Gly Asp Asn Ala Thr Val Ala Ala Gly His Ala Thr Leu
                85                  90                  95

Arg Glu His Leu Arg Asp Ile Lys Ala Glu Asn Thr Asp Ala Asn Phe
            100                 105                 110

Tyr Val Cys Pro Pro Pro Thr Gly Ala Thr Val Val Gln Phe Glu Gln
            115                 120                 125

Pro Arg Arg Cys Pro Thr Arg Pro Glu Gly Gln Asn Tyr Thr Glu Gly
130                 135                 140

Ile Ala Val Val Phe Lys Glu Asn Ile Ala Pro Tyr Lys Phe Lys Ala
145                 150                 155                 160

Thr Met Tyr Tyr Lys Asp Val Thr Val Ser Gln Val Trp Phe Gly His
                165                 170                 175

Arg Tyr Ser Gln Phe Met Gly Ile Phe Glu Asp Arg Ala Pro Val Pro
            180                 185                 190

Phe Glu Glu Val Ile Asp Lys Ile Asn Ala Lys Gly Val Cys Arg Ser
            195                 200                 205

Thr Ala Lys Tyr Val Arg Asn Asn Leu Glu Thr Thr Ala Phe His Arg
210                 215                 220

Asp Asp His Glu Thr Asp Met Glu Leu Lys Pro Ala Asn Ala Ala Thr
225                 230                 235                 240

Arg Thr Ser Arg Gly Trp His Thr Thr Asp Leu Lys Tyr Asn Pro Ser
                245                 250                 255

Arg Val Glu Ala Phe His Arg Tyr Gly Thr Thr Val Asn Cys Ile Val
            260                 265                 270

Glu Glu Val Asp Ala Arg Ser Val Tyr Pro Tyr Asp Glu Phe Val Leu
            275                 280                 285

Ala Thr Gly Asp Phe Val Tyr Met Ser Pro Phe Tyr Gly Tyr Arg Glu
290                 295                 300

Gly Ser His Thr Glu His Thr Ser Tyr Ala Ala Asp Arg Phe Lys Gln
305                 310                 315                 320

Val Asp Gly Phe Tyr Ala Arg Asp Leu Thr Thr Lys Ala Arg Ala Thr
                325                 330                 335

Ala Pro Thr Thr Arg Asn Leu Leu Thr Thr Pro Lys Phe Thr Val Ala
            340                 345                 350

Trp Asp Trp Val Pro Lys Arg Pro Ser Val Cys Thr Met Thr Lys Trp
            355                 360                 365

Gln Glu Val Asp Glu Met Leu Arg Ser Glu Tyr Gly Gly Ser Phe Arg
370                 375                 380

Phe Ser Ser Asp Ala Ile Ser Thr Thr Phe Thr Asn Leu Thr Glu
385                 390                 395                 400

Tyr Pro Leu Ser Arg Val Asp Leu Gly Asp Cys Ile Gly Lys Asp Ala
                405                 410                 415
```

```
Arg Asp Ala Met Asp Arg Ile Phe Ala Arg Arg Tyr Asn Ala Thr His
            420                 425                 430
Ile Lys Val Gly Gln Pro Gln Tyr Tyr Leu Ala Asn Gly Gly Phe Leu
            435                 440                 445
Ile Ala Tyr Gln Pro Leu Leu Ser Asn Thr Leu Ala Glu Leu Tyr Val
            450                 455                 460
Arg Glu His Leu Arg Glu Gln Ser Arg Lys Pro Pro Asn Pro Thr Pro
465                 470                 475                 480
Pro Pro Pro Gly Ala Ser Ala Asn Ala Ser Val Glu Arg Ile Lys Thr
                485                 490                 495
Thr Ser Ser Ile Glu Phe Ala Arg Leu Gln Phe Thr Tyr Asn His Ile
            500                 505                 510
Gln Arg His Val Asn Asp Met Leu Gly Arg Val Ala Ile Ala Trp Cys
            515                 520                 525
Glu Leu Gln Asn His Glu Leu Thr Leu Trp Asn Glu Ala Arg Lys Leu
            530                 535                 540
Asn Pro Asn Ala Ile Ala Ser Ala Thr Val Gly Arg Arg Val Ser Ala
545                 550                 555                 560
Arg Met Leu Gly Asp Val Met Ala Val Ser Thr Cys Val Pro Val Ala
                565                 570                 575
Ala Asp Asn Val Ile Val Gln Asn Ser Met Arg Ile Ser Ser Arg Pro
            580                 585                 590
Gly Ala Cys Tyr Ser Arg Pro Leu Val Ser Phe Arg Tyr Glu Asp Gln
            595                 600                 605
Gly Pro Leu Val Glu Gly Gln Leu Gly Glu Asn Asn Glu Leu Arg Leu
            610                 615                 620
Thr Arg Asp Ala Ile Glu Pro Cys Thr Val Gly His Arg Arg Tyr Phe
625                 630                 635                 640
Thr Phe Gly Gly Gly Tyr Val Tyr Phe Glu Glu Tyr Ala Tyr Ser His
                645                 650                 655
Gln Leu Ser Arg Ala Asp Ile Thr Thr Val Ser Thr Phe Ile Asp Leu
            660                 665                 670
Asn Ile Thr Met Leu Glu Asp His Glu Phe Val Pro Leu Glu Val Tyr
            675                 680                 685
Thr Arg His Glu Ile Lys Asp Ser Gly Leu Leu Asp Tyr Thr Glu Val
            690                 695                 700
Gln Arg Arg Asn Gln Leu His Asp Leu Arg Phe Ala Asp Ile Asp Thr
705                 710                 715                 720
Val Ile His Ala Asp Ala Asn Ala Ala Met Phe Ala Gly Leu Gly Ala
                725                 730                 735
Phe Phe Glu Gly Met Gly Asp Leu Gly Arg Ala Val Gly Lys Val Val
            740                 745                 750
Met Gly Ile Val Gly Gly Val Val Ser Ala Val Ser Gly Val Ser Ser
            755                 760                 765
Phe Met Ser Asn Pro Phe Gly Ala Leu Ala Val Gly Leu Leu Val Leu
            770                 775                 780
Ala Gly Leu Ala Ala Ala Phe Phe Ala Phe Arg Tyr Val Met Arg Leu
785                 790                 795                 800
Gln Ser Asn Pro Met Lys Ala Leu Tyr Pro Leu Thr Thr Lys Glu Leu
                805                 810                 815
Lys Asn Pro Thr Asn Pro Asp Ala Ser Gly Glu Gly Glu Glu Gly Gly
            820                 825                 830
```

```
Asp Phe Asp Glu Ala Lys Leu Ala Glu Ala Arg Glu Met Ile Arg Tyr
            835                 840                 845

Met Ala Leu Val Ser Ala Met Glu Arg Thr Glu His Lys Ala Lys Lys
    850                 855                 860

Lys Gly Thr Ser Ala Leu Leu Ser Ala Lys Val Thr Asp Met Val Met
865                 870                 875                 880

Arg Lys Arg Arg Asn Thr Asn Tyr Thr Gln Val Pro Asn Lys Asp Gly
                885                 890                 895

Asp Ala Asp Glu Asp Asp Leu
            900

<210> SEQ ID NO 12
<211> LENGTH: 904
<212> TYPE: PRT
<213> ORGANISM: Herpes Simplex Virus 1 strain KOS

<400> SEQUENCE: 12

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Thr Ser Pro Gly Thr Pro Gly Val Ala Ala Ala Thr Gln Ala Ala Asn
        35                  40                  45

Gly Gly Pro Ala Thr Pro Ala Pro Pro Leu Gly Ala Ala Pro Thr
50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300
```

```
Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
                340                 345                 350

Ala Trp Asp Trp Val Pro Lys Arg Pro Ser Val Cys Thr Met Thr Lys
                355                 360                 365

Trp Gln Glu Val Asp Glu Met Leu Arg Ser Glu Tyr Gly Gly Ser Phe
370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
                420                 425                 430

His Ile Lys Val Gly Gln Pro Gln Tyr Tyr Gln Ala Asn Gly Gly Phe
                435                 440                 445

Leu Ile Ala Tyr Gln Pro Leu Leu Ser Asn Thr Leu Ala Glu Leu Tyr
450                 455                 460

Val Arg Glu His Leu Arg Glu Gln Ser Arg Lys Pro Pro Asn Pro Thr
465                 470                 475                 480

Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
                500                 505                 510

Ile Gln Arg His Val Asn Asp Met Leu Gly Arg Val Ala Ile Ala Trp
                515                 520                 525

Cys Glu Leu Gln Asn His Glu Leu Thr Leu Trp Asn Glu Ala Arg Lys
                530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
                580                 585                 590

Pro Gly Ala Cys Tyr Ser Arg Pro Leu Val Ser Phe Arg Tyr Glu Asp
                595                 600                 605

Gln Gly Pro Leu Val Glu Gly Gln Leu Gly Glu Asn Asn Glu Leu Arg
                610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
                660                 665                 670

Leu Asn Ile Thr Met Leu Glu Asp His Glu Phe Val Pro Leu Glu Val
                675                 680                 685

Tyr Thr Arg His Glu Ile Lys Asp Ser Gly Leu Leu Asp Tyr Thr Glu
                690                 695                 700

Val Gln Arg Arg Asn Gln Leu His Asp Leu Arg Phe Ala Asp Ile Asp
705                 710                 715                 720
```

```
Thr Val Ile His Ala Asp Ala Asn Ala Ala Met Phe Ala Gly Leu Gly
            725                 730                 735

Ala Phe Phe Glu Gly Met Gly Asp Leu Gly Arg Ala Val Gly Lys Val
        740                 745                 750

Val Met Gly Ile Val Gly Val Val Ser Ala Val Ser Gly Val Ser
    755                 760                 765

Ser Phe Met Ser Asn Pro Phe Gly Ala Leu Ala Val Gly Leu Leu Val
770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Leu
            900

<210> SEQ ID NO 13
<211> LENGTH: 904
<212> TYPE: PRT
<213> ORGANISM: Herpes Simplex Virus 1 strain gC-39-R6

<400> S

```
Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
        290                 295                 300

Glu Gly Ser His Thr Glu His Thr Ser Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
        370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Leu Ala Asn Gly Gly Phe
        435                 440                 445

Leu Ile Ala Tyr Gln Pro Leu Leu Ser Asn Thr Leu Ala Glu Leu Tyr
        450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln His His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
        530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605
```

```
Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900

<210> SEQ ID NO 14
<211> LENGTH: 904
<212> TYPE: PRT
<213> ORGANISM: Herpes Simplex Virus 2 strain HG52

<400> SEQUENCE: 14

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
            20                  25                  30

Ser Gly Gly Val Ala Ala Thr Val Ala Ala Asn Gly Gly Pro Ala Ser
        35                  40                  45

Arg Pro Pro Pro Val Pro Ser Pro Ala Thr Thr Lys Ala Arg Lys Arg
    50                  55                  60

Lys Thr Lys Lys Pro Pro Lys Arg Pro Glu Ala Thr Pro Pro Pro Asp
65                  70                  75                  80
```

```
Ala Asn Ala Thr Val Ala Ala Gly His Ala Thr Leu Arg Ala His Leu
             85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
            115                 120                 125

Pro Thr Arg Pro Glu Gly Gln Asn Tyr Thr Glu Gly Ile Ala Val Val
130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Thr Lys Gly Val Cys Arg Ser Thr Ala Lys Tyr
            195                 200                 205

Val Arg Asn Asn Met Glu Thr Thr Ala Phe His Arg Asp Asp His Glu
            210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Asn Cys Ile Val Glu Glu Val Asp
            260                 265                 270

Ala Arg Ser Val Tyr Pro Tyr Asp Glu Phe Val Leu Ala Thr Gly Asp
            275                 280                 285

Phe Val Tyr Met Ser Pro Phe Tyr Gly Tyr Arg Glu Gly Ser His Thr
            290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
            340                 345                 350

Pro Lys Arg Pro Ala Val Cys Thr Met Thr Lys Trp Gln Glu Val Asp
            355                 360                 365

Glu Met Leu Arg Ala Glu Tyr Gly Gly Ser Phe Arg Phe Ser Ser Asp
            370                 375                 380

Ala Ile Ser Thr Thr Phe Thr Thr Asn Leu Thr Glu Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
            420                 425                 430

Gln Pro Gln Tyr Tyr Leu Ala Thr Gly Gly Phe Leu Ile Ala Tyr Gln
            435                 440                 445

Pro Leu Leu Ser Asn Thr Leu Ala Glu Leu Tyr Val Arg Glu Tyr Met
450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495
```

```
Ser Ile Glu Phe Ala Arg Leu Gln Phe Thr Tyr Asn His Ile Gln Arg
            500                 505                 510

His Val Asn Asp Met Leu Gly Arg Ile Ala Val Ala Trp Cys Glu Leu
        515                 520                 525

Gln Asn His Glu Leu Thr Leu Trp Asn Glu Ala Arg Lys Leu Asn Pro
    530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765

Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Arg
    850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900
```

<210> SEQ ID NO 15
<211> LENGTH: 904
<212> TYPE: PRT
<213> ORGANISM: Herpes Simplex Virus 2 strain 333

<400> SEQUENCE: 15

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
            20                  25                  30

Ser Gly Gly Val Ala Ala Thr Val Ala Ala Asn Gly Gly Pro Ala Ser
        35                  40                  45

Arg Pro Pro Val Pro Ser Pro Ala Thr Thr Lys Ala Arg Lys Arg
50                  55                  60

Lys Thr Lys Lys Pro Pro Lys Arg Pro Glu Ala Thr Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                 200                 205

Val Arg Asn Asn Met Glu Thr Thr Ala Phe His Arg Asp Asp His Glu
210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Thr Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
            340                 345                 350

Pro Lys Arg Pro Ala Val Cys Thr Met Thr Lys Trp Gln Glu Val Asp
        355                 360                 365

Glu Met Leu Arg Ala Glu Tyr Gly Gly Ser Phe Arg Phe Ser Ser Asp
370                 375                 380

```
Ala Ile Ser Thr Thr Phe Thr Thr Asn Leu Thr Gln Tyr Ser Leu Ser
385                 390                 395                 400

Arg Val Asp Leu Gly Asp Cys Ile Gly Arg Asp Ala Arg Glu Ala Ile
            405                 410                 415

Asp Arg Met Phe Ala Arg Lys Tyr Asn Ala Thr His Ile Lys Val Gly
            420                 425                 430

Gln Pro Gln Tyr Tyr Leu Ala Thr Gly Gly Phe Leu Ile Ala Tyr Gln
            435                 440                 445

Pro Leu Leu Ser Asn Thr Leu Ala Glu Leu Tyr Val Arg Glu Tyr Met
        450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
            485                 490                 495

Ser Ile Glu Phe Ala Arg Leu Gln Phe Thr Tyr Asn His Ile Gln Arg
            500                 505                 510

His Val Asn Asp Met Leu Gly Arg Ile Ala Val Ala Trp Cys Glu Leu
        515                 520                 525

Gln Asn His Glu Leu Thr Leu Trp Asn Glu Ala Arg Lys Leu Asn Pro
        530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
            565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
        610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
            645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Gly Val Tyr Thr Arg
            675                 680                 685

His Glu Ile Lys Asp Ser Gly Leu Leu Asp Tyr Thr Glu Val Gln Arg
        690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
            725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
            755                 760                 765

Ser Asn Pro Phe Gly Ala Leu Ala Val Gly Leu Leu Val Leu Ala Gly
        770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
```

```
               805                 810                 815
Ser Asp Pro Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Arg
            850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900

<210> SEQ ID NO 16
<211> LENGTH: 901
<212> TYPE: PRT
<213> ORGANISM: Herpes Simplex Virus 2 strain MMA

<400> SEQUENCE: 16

Met Arg Gly Gly Gly Leu Ile Cys Ala Leu Val Val Gly Ala Leu Val
1               5                   10                  15

Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Arg Pro Pro
        35                  40                  45

Pro Val Pro Ser Pro Ala Thr Thr Arg Ala Arg Lys Arg Lys Thr Lys
    50                  55                  60

Lys Pro Pro Glu Arg Pro Glu Ala Thr Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270
```

```
Val Tyr Pro Tyr Asp Glu Phe Val Leu Ala Thr Gly Asp Phe Val Tyr
            275                 280                 285

Met Ser Pro Phe Tyr Gly Tyr Arg Glu Gly Ser His Thr Glu His Thr
290                 295                 300

Ser Tyr Ala Ala Asp Arg Phe Lys Gln Val Asp Gly Phe Tyr Ala Arg
305                 310                 315                 320

Asp Leu Thr Thr Lys Ala Gln Ala Thr Ser Pro Thr Thr Arg Asn Leu
                325                 330                 335

Leu Thr Thr Pro Lys Phe Thr Val Ala Trp Asp Trp Val Pro Lys Arg
                340                 345                 350

Pro Ala Val Cys Thr Met Thr Lys Trp Gln Glu Val Asp Glu Met Leu
                355                 360                 365

Arg Ala Glu Tyr Gly Gly Ser Phe Arg Phe Ser Ser Asp Ala Ile Ser
370                 375                 380

Thr Thr Phe Thr Thr Asn Leu Thr Glu Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
                420                 425                 430

Tyr Tyr Leu Ala Thr Gly Gly Phe Leu Ile Ala Tyr Gln Pro Leu Leu
                435                 440                 445

Ser Asn Thr Leu Ala Glu Leu Tyr Val Arg Glu Tyr Met Arg Glu Gln
                450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
                500                 505                 510

Asp Met Leu Gly Arg Ile Ala Val Ala Trp Cys Glu Leu Gln Asn His
                515                 520                 525

Glu Leu Thr Leu Trp Asn Glu Ala Arg Lys Leu Asn Pro Asn Ala Ile
                530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
                580                 585                 590

Arg Pro Leu Val Ser Phe Arg Tyr Glu Asp Gln Gly Pro Leu Ile Glu
                595                 600                 605

Gly Gln Leu Gly Glu Asn Asn Glu Leu Arg Leu Thr Arg Asp Ala Leu
                610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
                660                 665                 670

Glu Asp His Glu Phe Val Pro Leu Glu Val Tyr Thr Arg His Glu Ile
                675                 680                 685

Lys Asp Ser Gly Leu Leu Asp Tyr Thr Glu Val Gln Arg Arg Asn Gln
```

-continued

```
            690                 695                 700
Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met
                725                 730                 735

Gly Asp Leu Gly Arg Ala Val Gly Lys Val Val Met Gly Val Val Gly
                740                 745                 750

Gly Val Val Ser Ala Val Ser Gly Val Ser Ser Phe Met Ser Asn Pro
            755                 760                 765

Phe Gly Ala Leu Ala Val Gly Leu Leu Val Leu Ala Gly Leu Val Ala
        770                 775                 780

Ala Phe Phe Ala Phe Arg Tyr Val Leu Gln Leu Gln Arg Asn Pro Met
785                 790                 795                 800

Lys Ala Leu Tyr Pro Leu Thr Thr Lys Glu Leu Lys Thr Ser Asp Pro
                805                 810                 815

Gly Gly Val Gly Gly Glu Gly Glu Glu Gly Ala Glu Gly Gly Gly Phe
                820                 825                 830

Asp Glu Ala Lys Leu Ala Glu Ala Arg Glu Met Ile Arg Tyr Met Ala
            835                 840                 845

Leu Val Ser Ala Met Glu Arg Thr Glu His Lys Ala Arg Lys Lys Gly
        850                 855                 860

Thr Ser Ala Leu Leu Ser Ser Lys Val Thr Asn Met Val Leu Arg Lys
865                 870                 875                 880

Arg Asn Lys Ala Arg Tyr Ser Pro Leu His Asn Glu Asp Glu Ala Gly
                885                 890                 895

Asp Glu Asp Glu Leu
                900
```

TOPICAL APPLICATION FOR AN ANTI-HSV ANTIBODY

CROSS-REFERENCE TO RELATED APPLICATIONS

This application is a § 371 National Stage Application of PCT/EP2015/064378, filed 25 Jun. 2015, which claims priority to EP 14174174.4, filed 26 Jun. 2014. These documents (PCT/EP2015/064378 and EP 14174174.4) are hereby incorporated by reference in their entirety.

The present invention relates to an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered as well as to a pharmaceutical composition comprising an effective amount of said antibody or antigen-binding fragment thereof and at least one pharmaceutically acceptable excipient.

Herpes simplex virus (HSV) refers to two closely related members of the herpesviridae family, Herpes simplex virus type 1 (HSV-1) and Herpes simplex virus type 2 (HSV-2). HSV-1 and HSV-2 are among the most common viral infections in the world. HSV-1 infections are often acquired in early childhood as subclinical infections while a subset present with severe disease. HSV-2 is usually acquired through sexual activity and mainly causes lesions in the genital area. Infection with the herpes virus is categorized into one of several distinct disorders based on the site of infection. Oral herpes (Herpes simplex labialis), the visible symptoms of which are colloquially called cold sores or fever blisters, is an infection of the face or mouth. Oral herpes is the most common form of infection. Genital herpes (Herpes simplex genitalis) is the second most common form of herpes. Other disorders such as herpetic whitlow, herpes gladiatorum, ocular herpes (Herpes simplex conreae or Herpes simplex Keratitis), cerebral herpes infection encephalitis, Mollaret's meningitis, neonatal herpes, and possibly Bell's palsy are all caused by herpes simplex viruses.

After primary infection HSV spreads from infected epithelial cells to axons of sensory neurons innervating the site of the primary infection followed by retrograde transport to the respective dorsal root ganglia, where HSV establishes a latent reservoir for life. HSV infection of neurons exists as a reversible state and episodes of viral reactivation (outbreaks) may occur from time to time. Reactivation of the virus can be triggered by a wide range of stress stimuli (e.g. immunodeficiency, trauma, fever, menstruation, UV light and sexual intercourse) that act on the neuron, or at a peripheral site innervated by the infected ganglion, or systemically. Intermittent HSV reactivations result in the production of infectious HSV from latently infected neurons. Once reactivated the virus is transported by the neuron back to the nerve terminals in the epithelium.

The pathology of HSV infections is mainly caused by a direct cytopathic effect of the virus, resulting in cellular lysis and focal necrosis of the infected area. Herpes simplex is most easily transmitted by direct contact with a lesion or the body fluid of an infected individual. Oral herpes is easily diagnosed if the patient presents with visible sores or ulcers. Transmission may also occur through skin-to-skin contact during periods of asymptomatic shedding. Although most individuals infected with genital herpes are asymptomatic, severe clinical manifestations, especially in populations with underlying immune compromising conditions, can occur. HSV-2 increases the risk of HIV acquisition by two to three-fold as well as HIV transmission in dually infected individuals. In addition, genital herpes can be perinatally transmitted and cause life-threatening neonatal HSV infection. Barrier protection methods are the most reliable method of preventing transmission of herpes, but they merely reduce rather than eliminate risk.

A cure for herpes has not yet been developed. Once infected, the virus remains in the body for life. Recurrent infections (outbreaks) may occur from time to time. However, after several years, outbreaks become less severe and more sporadic, and some people will become perpetually asymptomatic and will no longer experience outbreaks, though they may still be contagious to others. Treatments with antivirals can reduce viral shedding and alleviate the severity of symptomatic episodes.

Herpes simplex labialis (also called cold sores, herpes simplex labialis, recurrent herpes labialis, or orolabial herpes) is a type of herpes simplex occurring on the lip, i.e., an infection caused by herpes simplex virus (HSV). An outbreak typically causes small blisters or sores on or around the mouth commonly known as cold sores or fever blisters. The sores typically heal within 2 to 3 weeks, but the herpes virus remains dormant in the facial nerves, following orofacial infection, periodically reactivating (in symptomatic people) to create sores in the same area of the mouth or face at the site of the original infection. Cold sore has a rate of frequency that varies from rare episodes to 12 or more recurrences per year. People with the condition typically experience one to three attacks annually. The frequency and severity of outbreaks generally decreases over time.

Herpes simplex genitalis (or genital herpes) is a genital infection caused by the herpes simplex virus. A 1998 study indicated it was the most common sexually transmitted infection by the number of cases. Most individuals carrying herpes are unaware they have been infected and many will never suffer an outbreak, which involves blisters similar to cold sores. While there is no cure for herpes, over time symptoms are increasingly mild and outbreaks are decreasingly frequent. As mentioned, HSV has been classified into two distinct categories, HSV-1 and HSV-2. Although genital herpes was previously caused primarily by HSV-2, genital HSV-1 infections are increasing and now cause up to 80% of infections. When symptomatic, the typical manifestation of a primary HSV-1 or HSV-2 genital infection is clusters of genital sores consisting of inflamed papules and vesicles on the outer surface of the genitals, resembling cold sores. These usually appear 4-7 days after sexual exposure to HSV for the first time. Genital HSV-1 infection recurs at rate of about one sixth of that of genital HSV-2.

Herpetic simplex keratitis is an inflammation of the eye predominantly caused by recurrent HSV infection of the cornea. Ocular infection with HSV can cause eye disease of different severity, ranging from conjunctivitis and dendritic keratitis to stromal edema and necrotizing stromal keratitis. HSV-1 causes more than 90% of ocular HSV infections and is the leading cause of viral-induced blindness in developed countries.

Moreover, there are other, rather rare HSV infections of mucosal or epidermal tissue which will be briefly addressed in the following.

Chronic or disseminated cutaneous herpes simplex infections are known which are not restricted to labial or genital tract. Mostly, immunodeficient patients are affected with this disease like, e.g., patients with Hypogammaglobulinema or patients with cutaneous T-cell lymphomas. Chronic cutaneous herpes simplex is a distinctive clinical presentation of the herpes simplex virus (HSV) in a compromised host. This infection can be defined as chronically active destructive skin lesions that potentially may progress into the disseminated (systemic) form. While most HSV infections display episodes that show healing in one or two weeks, the lesions of chronic cutaneous herpes simplex have an indolent course that may last for several months. Chronic cutaneous herpes simplex, which is common in immunosuppressed patients, is characterized by atypical, chronic, and persistent lesions, which complicate and delay the diagnosis. This may lead to death caused by associated complications. It is of vital importance that when evaluating chronic ulcers of long duration, especially in children, the possibility of a chronic herpes simplex virus infection be considered. Herpes gladiatorum refers to a herpes skin infection that occurs in adolescence among wrestlers but it is also common in other contact sports. It usually occurs on the head, most commonly the jaw area, the neck, chest, face, stomach, and legs. Eczema herpeticum, also known as a form of Kaposi varicelliform eruption caused by viral infection, usually with the herpes simplex virus (HSV), is an extensive cutaneous vesicular eruption that arises from pre-existing skin disease, usually atopic dermatitis (AD). Children with AD have a higher risk of developing eczema herpeticum, in which HSV type 1 (HSV-1) is the most common pathogen. Eczema herpeticum can be severe, progressing to disseminated infection and death if untreated.

Diseases caused by HSV, in particular Herpes simplex labialis and Herpes simplex genitalis represent the most common infectious diseases of the skin.

At present, it is standard to use virustatic agents in antiviral HSV therapy. The most common virustatic agents (e.g., aciclovir, penciclovir, foscarnet, idoxuridin) are nucleoside or pyrophosphate analogues whose common active principle is based on the inhibition of DNA synthesis in virus-infected cells. In other words, these virustatic agents are only effective in infected cells while the virus is actively replicating. In a double blinded placebo-controlled study with 1385 patients suffering from acute Herpes simplex labialis infection, it has been demonstrated that Aciclovir (in the form of Zovirax Creme) is capable of reducing the infection by 0.5 days (i.e., from 5 days to 4.5 days) upon 5× daily administration for 4 days compared to placebo-treated patients. Moreover, such a treatment suffers from the disadvantage that the development of lesions which are typical for Herpes cannot be prevented.

Recently, a murine and a correspondingly humanized antibody has been described which specifically recognizes the glycoprotein B (gB) of HSV type 1 (HSV-1) and HSV-2. HSV-gB is an integral part of the multicomponent fusion system required for virus entry and cell-cell fusion. This antibody, the monoclonal antibody MAb 2c, has been demonstrated to neutralize the virus by abrogating viral cell-to-cell spread, a key mechanism by which HSV-1/2 escapes humoral immune surveillance independent from antibody-dependent cellular cytotoxicity (ADCC) and/or complement-dependent cytotoxicity (CDC); Eis-Hübinger et al., Intervirology 32:351-360 (1991); Eis-Hübinger et al., Journal of General Virology 74:379-385 (1993); WO2011/038933 A2; Krawczyk A, et al., Journal of virology (2011); 85(4):1793-1803; Krawczyk A, et al., Proc Natl Acad Sci USA (2013); 110(17):6760-6765.

However, these antibodies have only been administered systemically (i.e., by, e.g., intravenous, intramuscular or subcutaneous administration) in line with the rationale excluding oral administration of antibodies due to their size, hydrophilic nature and degradation in the stomach. Thus, the prior art antibodies have not been administered locally on the surface of the skin but only systematically.

WO 2005/023303 discloses a method for the treatment of HSV by an intravenous administration of IgA fractions of human serum or IgG fractions of human plasma while a topical administration as well as the diseases herpes labialis and herpes genitalis are mentioned.

Although topical administration of antibodies has previously been described, such an application has only been suggested for prophylactic use in the prevention of sexually transmitted HSV-2 diseases. Sherwood et al., Nat. Biotechnol. 14(4):468-471 (1996) describe the prophylactic topical passive immunoprotection of female mice against genital herpes in a mouse model of vaginally-transmitted HSV-2 infection by a monoclonal antibody to HSV-2. Similarly, Zeitlin et al., Virology 225(1):213-215 (1996), Zeitlin et al., Contraception 56(5):329-335 (1997), Zeitlin et al., J. Reprod. Immunol. 40(1):93-101 (1998) and Zeitlin et al., Nat. Biotechnol. 16(13):1361-1364 (1998) describe the prophylactic topical administration of anti-HSV-2 antibodies in the prevention of sexually transmission of HSV-2.

Moreover, the TNF-alpha antibody infliximab has previously been described to improve the healing of chronic wounds upon topical application (Streit et al., International Wound Journal 3(3):171-179 (2006)) while the topical application of polyclonal and monoclonal antibodies against *Pseudomonas aeruginosa* has previously been described (U.S. Pat. No. 4,994,269). Furthermore, Clement et al., ARVO, Abstract/Poster 6155/D1015 describes the topical administration of an antibody targeting phosphatidylserine (PS) in a rabbit model of acute HSV-1 Keratitis while Yu et al., Eye Science 12(3):145-150 (1996) describe the topical use of anti-HSV monoclonal glycoprotein antibodies in acute herpetic Keratitis of rabbits infected by HSV-1. WO 2010/128053 describes the use of an antibody fragment binding to the viral surface antigen glycoprotein D neutralizing HSV-1 and HSV-2 for ocular topical administration for treating ocular diseases like ocular keratitis.

Thus, there is a need to provide improved means and methods for the treatment of acute Herpes simplex infections which facilitates administration regimens known in the art and prevents local spreading of the infection.

The present invention provides an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered as well as to a pharmaceutical composition comprising an effective amount of said antibody or antigen-binding fragment thereof and at least one pharmaceutically acceptable excipient.

Surprisingly, the present invention demonstrates that the topical administration of a humanized anti-HSV antibody in an acute infection of the tissue of the lips upon HSV-infection eliminates the infection within 24 hours while the local spreading of the Herpes infection via cell-to-cell spread is prevented, thereby avoiding the generation of lesions. In contrast to the above-described virustatic agents used in the treatment of viral infections like Herpes simplex labialis the anti-HSV antibody of the present invention is capable of rapidly neutralizing the virus by a mechanism which is independent of viral replication. Beneficially, the antibody of the invention is demonstrated to suppress the lytic route of the virus, thereby preventing skin lesions.

In view of the prior art, the technical problem underlying the present invention is the provision of improved means and methods for the treatment of acute Herpes simplex infections which facilitates administration regimens known in the art and prevents local spreading of the infection.

The technical problem is solved by provision of the embodiments characterized in the claims.

The present invention relates to an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered.

As mentioned above, it has surprisingly been demonstrated in the appended examples that the topical administration of a humanized anti-HSV antibody in an acute infection of the tissue of the lips upon HSV-infection rapidly eliminates the infection within 24 hours while the local spreading of the Herpes infection via cell-to-cell spread is prevented, thereby avoiding the generation of lesions.

This finding is in particular surprising and unexpected in light of the prior art discussed above relating to the systemic administration as described in Eis-Hübinger et al., Intervirology 32:351-360 (1991); Eis-Hübinger et al., Journal of General Virology 74:379-385 (1993); WO2011/038933 A2; Krawczyk A, et al., Journal of virology (2011); 85(4):1793-1803; Krawczyk A, et al., Proc Natl Acad Sci USA (2013); 110(17):6760-6765; the prophylactic treatment as described in Sherwood et al., Nat. Biotechnol. 14(4):468-471 (1996); Zeitlin et al., Virology 225(1):213-215 (1996); Zeitlin et al., Contraception 56(5):329-335 (1997); Zeitlin et al., J. Reprod. Immunol. 40(1):93-101 (1998) and Zeitlin et al., Nat. Biotechnol. 16(13):1361-1364 (1998); and the topical treatment with an anti-HSV glycoprotein antibody in acute Herpes simplex keratitis infection as described in Yu et al., Eye Science 12(3):145-150 (1996) (and Clement et al., ARVO, Abstract/Poster 6155/D1015; as well as WO 2010/128053) for the following reasons.

In contrast to the prior art, it has been demonstrated that the topical administration of a humanized anti-HSV antibody in an acute infection of the tissue of the lips upon HSV-infection rapidly eliminates the infection within 24 hours while the local spreading of the Herpes infection via cell-to-cell spread is prevented, thereby avoiding the generation of lesions.

The surprising nature of this finding, i.e., that a humanized anti-HSV antibody or fragment thereof can be used in the topical therapy of recurrent HSV infections of epithelia of mucosa or skin is, in particular surprising and unexpected taking into account basic knowledge about the epidermis structure.

The layers of human skin epithelium and mucous membrane epithelia physically separate the organism from its environment and serve as its first line of structural and functional defense against dehydration, chemical substances, physical insults and micro-organisms. Highly polarized epithelial cells form the apical layers of the epidermis and less differentiated cells the basal region, where the epidermal progenitor cells reside. Occluding junctions, so called tight junctions (TJ), located at the lateral plasma membranes of the most superficial living layer, the stratum granulosum (Brandner, et al., 2002 Eur J Cell Biol 81, 253-263; Furuse et al., 2002, J Cell Biol 156, 1099-1111) secure the epidermal barrier function between the apical layer (stratum corneum) and the basolateral layers (stratum spinosum, stratum basale & lamina basale).

The principal site of HSV replication and progeny virus production in the skin are the less differentiated, proliferating keratinocytes of the basal region (stratum basale) (Mingo et al., 2012, J Virol 86, 7084-7097; Schelhaas et al., 2003, J Gen Virol 84, 2473-2484).

Pathogenesis of primary infection requires that HSV accesses permissive nucleated cells in the mid- to basal epidermis via microscopic breaches in the epidermis that occur for instance with coitus.

Reactivation of the HSV genome from latency within ganglia leads to transport of newly formed virions traffic down axon microtubules for release at synaptic terminals at the dermal-epidermal junction or within the mid-layer of the epidermis (Diefenbach et al., 2008, Rev Med Virol 18, 35-51). HSV needs to cross the axonal-epithelial gap for subsequent replication in the basal region of the epidermis.

Humoral immunity plays an important role in controlling HSV infection. Circulating serum antibodies, which can bind viral envelope glycoproteins necessary for viral entry, develop during infection (Cohen et al., 1984, Journal of virology 49, 102-108). It has been shown that the presence of maternal serum antibodies specific to HSV reduces neonatal transmission of HSV-2 (Brown et al., 1991, N Engl J Med 324, 1247-1252). Neutralizing serum antibodies are capable of binding virus in the gap between neuron endings and epithelial cells and limit bidirectional viral transfer between these tissues (Mikloska et al., 1999, Journal of virology 73, 5934-5944). Evidently, serum antibodies or systemically applied antibodies limit the extent of HSV infection.

Tight junctions (TJ), however, which are restricted to the stratum granulosum, form a barrier for larger molecules (Helfrich et al., 2007, J Invest Dermatol 127, 782-791; Mertens et al., 2005, J Cell Biol 170, 1029-1037; Yuki et al., 2007, Exp Dermatol 16, 324-330). Therefore, it was utmost surprising that topical application of a large molecule like an antibody to the outer skin is able to eradicate a recurrent HSV infection effectively and prevents formation of lesions. Thus, for this reason, it was surprising vis-á-vis a systemic administration, that a local, topical administration rapidly eliminates the infection as exemplified in the examples.

Moreover, although the prior art describes the protection of sexually transmitted primary HSV-2 infection by a topical prophylactic application of anti-HSV antibodies the treatment of an acute infection is surprising because in the experimental setting of the prior art discussed above, anti-HSV antibodies were topically applied to the vagina before delivering the virus inoculum. The viral load is getting neutralized like in a two-dimensional in vitro neutralization assay, where neutralizing antibodies prevent attachment of free virus particles to target cells and virus replication actually does not take place. This is in stark contrast to the treatment of an acute infection which has surprisingly been shown to rapidly eliminate the infection by the topical administration of an antibody of the present invention as exemplified in the examples. Moreover, although the prior art describes the topical treatment with an anti-HSV glycoprotein antibody in acute Herpes simplex keratitis, an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered is surprising for the following reasons. The principal site of HSV replication and progeny virus production in the skin are the less differentiated, proliferating keratinocytes of the basal region (Mingo et al., 2012, J Virol 86, 7084-7097; Schelhaas et al., 2003, J Gen Virol 84, 2473-2484). It has been shown that tight junctions (TJ), which are restricted to the stratum granulosum, form a barrier for larger molecules (Helfrich et al., 2007, J Invest Dermatol 127, 782-791; Mertens et al., 2005, J Cell Biol 170, 1029-1037; Yuki et al., 2007, Exp Dermatol 16, 324-330). Therefore, it was utmost surprising that topical application of a large molecule like an antibody to the outer skin is able to eradicate a recurrent HSV infection effectively and prevents formation of lesions.

In contrast to skin epithelium and mucous membrane epithelia the cornea of the eye is a non-keratinized stratified squamous epithelium, which is exceedingly thin and consists of fast-growing and easily regenerated cells. All layers of the eye epithelium are constantly undergoing mitosis. The corneal epithelium provides a smooth surface that absorbs oxygen and cell nutrients from tears, then distributes these nutrients to the rest of the cornea. Another major difference to skin epithelium and mucous membrane epithelia is some degree of leakiness of the corneal endothelium, which is essential for nutrient diffusion. Ulturastructure studies of the corneal endothelium confirmed that gaps in specific tight junctions proteins exist and that the tight junctions of the cornea are "leaky" junctions (Barry et al., 1995, Invest Ophthalmol Vis Sci 36, 1115-1124; Noske et al., 1994, Ger J Ophthalmol 3, 253-257; Petroll et al., 1999, Curr Eye Res 18, 10-19). The cornea of the eye is an immunologically privileged site. The ocular surface is constantly covered by a tear film, which besides largely consisting of water although contains a number of proteins that have antiviral activity such as immunoglobulin A antibodies, lysozyme, complement and amylase. The presence of anti-HSV antibodies has been demonstrated in tears (Centifanto et al., 1970, Ann NY Acad Sci 173, 649-656; Fox et al., 1986, The British journal of ophthalmology 70, 584-588; Shani et al., 1985, Curr Eye Res 4, 103-111). Therefore, topical application of recombinant antibodies may be beneficial for the treatment of ocular herpes infections. However, for the above reasons, it was unexpected that topical application of a large molecule like an antibody to the outer skin is able to eradicate a recurrent HSV infection effectively and prevents formation of lesions.

The infections of mucosal or epidermal tissue to be treated with the anti-HSV antibody or an antigen-binding fragment which are caused by HSV-1 or HSV-2, i.e., the infections selected from the group consisting of Herpes simplex labialis, Herpes simplex genitalis, chronic or disseminated cutaneous herpes simplex infection, Herpes gladiatorum and Eczema herpeticum are well known to the person skilled in the art and represent well-defined diseases. As already mentioned above, Herpes simplex labialis (also called cold sores, herpes simplex labialis, recurrent herpes labialis, or orolabial herpes) is a type of herpes simplex occurring on the lip, i.e. an infection by herpes simplex virus (HSV). An outbreak typically causes small blisters or sores on or around the mouth commonly known as cold sores or fever blisters. The sores typically heal within 2 to 3 weeks, but the herpes virus remains dormant in the facial nerves, following orofacial infection, periodically reactivating (in symptomatic people) to create sores in the same area of the mouth or face at the site of the original infection. Cold sore has a rate of frequency that varies from rare episodes to 12 or more recurrences per year. People with the condition typically experience one to three attacks annually. The frequency and severity of outbreaks generally decreases over time.

Herpes simplex genitalis (or genital herpes) is a genital infection caused by the herpes simplex virus. A 1998 study indicated it was the most common sexually transmitted infection by the number of cases. Most individuals carrying herpes are unaware they have been infected and many will never suffer an outbreak, which involves blisters similar to cold sores. While there is no cure for herpes, over time symptoms are increasingly mild and outbreaks are decreasingly frequent. As mentioned, HSV has been classified into two distinct categories, HSV-1 and HSV-2. Although genital herpes was previously caused primarily by HSV-2, genital HSV-1 infections are increasing and now cause up to 80% of infections. When symptomatic, the typical manifestation of a primary HSV-1 or HSV-2 genital infection is clusters of genital sores consisting of inflamed papules and vesicles on the outer surface of the genitals, resembling cold sores. These usually appear 4-7 days after sexual exposure to HSV for the first time. Genital HSV-1 infection recurs at rate of about one sixth of that of genital HSV-2.

Chronic or disseminated cutaneous herpes simplex infections are known which are not restricted to labial or genital tract. Mostly, immunodeficient patients are affected with this disease like, e.g., patients with Hypogammaglobulinema or patients with cutaneous T-cell lymphomas. Chronic cutaneous herpes simplex is a distinctive clinical presentation of the herpes simplex virus (HSV) in a compromised host. This infection can be defined as chronically active destructive skin lesions that potentially may progress into the disseminated (systemic) form. While most HSV infections display episodes that show healing in one or two weeks, the lesions of chronic cutaneous herpes simplex have an indolent course that may last for several months. Chronic cutaneous herpes simplex, which is common in immunosuppressed patients, is characterized by atypical, chronic, and persistent lesions, which complicate and delay the diagnosis. This may lead to death caused by associated complications. It is of vital importance that when evaluating chronic ulcers of long duration, especially in children, the possibility of a chronic herpes simplex virus infection be considered.

Herpes gladiatorum is a herpes skin infection that occurs in adolescence among wrestlers but it is also common in other contact sports. It usually occurs on the head, most commonly the jaw area, the neck, chest, face, stomach, and legs.

Eczema herpeticum, also known as a form of Kaposi varicelliform eruption caused by viral infection, usually with the herpes simplex virus (HSV), is an extensive cutaneous vesicular eruption that arises from pre-existing skin disease, usually atopic dermatitis (AD). Children with AD have a higher risk of developing eczema herpeticum, in which HSV type 1 (HSV-1) is the most common pathogen. Eczema herpeticum can be severe, progressing to disseminated infection and death if untreated.

The antibody or fragment thereof as used in the context of the present invention for use in treating an acute infection of mucosal or epidermal tissue in a subject caused by HSV-1 or HSV-2 is not particularly limited as long as it is an "anti-HSV antibody or an antigen-binding fragment thereof". Thus, the antibody may be any antibody which specifically binds to or specifically recognizes or interacts with a HSV, i.e., a domain or an antigen of a HSV.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of the HSV. Said binding/interaction is also understood to define a "specific recognition". The term "specifically recognizing" means in accordance with this invention that the antibody is capable of specifically interacting with and/or binding to at least two amino acids of each of a HSV as defined herein. Antibodies can recognize, interact and/or bind to different epitopes on a HSV. This term relates to the specificity of the antibody molecule, i.e., to its ability to discriminate between the specific regions of a HSV.

The term "specific interaction" as used in accordance with the present invention means that the antibody or antigen-binding fragment thereof of the invention does not or does not essentially cross-react with (poly) peptides of similar structures. Accordingly, the antibody or antigen-binding fragment thereof of the invention specifically binds to/interacts with structures of a HSV, preferably HSV-1 or HSV-2. Specific examples of such molecules against which said first and second, Ig-derived domain is directed are given herein below.

Cross-reactivity of a panel of antibody or antigen-binding fragment thereof under investigation may be tested, for example, by assessing binding of said panel of antibody or antigen-binding fragment thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, antigen-binding fragments thereof and the like) that bind to the certain structure of the HSV, e.g., a specific epitope or (poly) peptide/protein of the HSV but do not or do not essentially bind to any of the other epitope or (poly) peptides of the same HSV, are considered specific for the epitope or (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays.

The term "binding to" does not only relate to a linear epitope but may also relate to a conformational epitope, a structural epitope or a discontinuous epitope consisting of two regions of the human target molecules or parts thereof. In the context of this invention, a conformational epitope is defined by two or more discrete amino acid sequences separated in the primary sequence which comes together on the surface of the molecule when the polypeptide folds to the native protein (Sela, *Science* 166 (1969), 1365 and Laver, *Cell* 61 (1990), 553-536). Moreover, the term "binding to" is interchangeably used in the context of the present invention with the terms "interacting with" or "recognizing".

Accordingly, specificity can be determined experimentally by methods known in the art and methods as described herein. Such methods comprise, but are not limited to Western Blots, ELISA-, RIA-, ECL-, IRMA-tests and peptide scans.

The treatment of the present invention relates to the treatment of acute infections. "Acute" in this respect means that the subject shows symptoms of the disease. In other words, the subject to be treated is in actual need of a treatment and the term "acute treatment" in the context of the present invention relates to the measures taken to actually treat the disease after the onset or the breakout of the disease. The term "acute" as referred to in the context of the present invention is opposed to a prophylactic treatment or preventive treatment, i.e., measures taken for disease prevention, e.g., in order to prevent the infection and/or the onset/outbreak of the disease. More specifically, prophylactic treatment may be understood in a way that it prevents attachment of free virus particles (from outside the body) to target cells and in turn prevents virus replication. In contrast, at an acute infection (which could be a primary or a recurrent infection) progeny virus have been raced upon HSV replication. Thus, the "acute treatment" referred to in the present invention does explicitly not relate to prophylactic or preventive treatment of an infection caused by HSV-1 or HSV-2.

Mucosal tissue that may display an acute infection refers to tissues of the mucous membranes which are linings of mostly endodermal origin, covered in epithelium, which are involved in absorption and secretion. They line cavities that are exposed to the external environment and internal organs. They are at several places contiguous with skin: e.g., at the nostrils, the lips of the mouth, the eyelids, the ears, the genital area, and the anus.

Epidermal tissue that may display an acute infection refers to tissues of the epidermis, i.e., the outermost layers of cells in the skin, which together with the dermis forms the cutis. The epidermis is a stratified squamous epithelium composed of proliferating basal and differentiated suprabasal keratinocytes which acts as the body's major barrier against an inhospitable environment, by preventing pathogens from entering, making the skin a natural barrier to infection. It also regulates the amount of water released from the body into the atmosphere through transepidermal water loss.

As mentioned, the anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum is to be topically administered.

The term "topical administration" in accordance with the present invention relates to a medication, application or administration that is applied to body surfaces such as the skin or mucous membranes to treat the infection referred to above via a large range of classes of forms of administration, including but not limited to creams, foams, gels, lotions and ointments. In a preferred embodiment, topical administration is understood to be epicutaneous, meaning that the anti-HSV antibody or an antigen-binding fragment thereof is applied directly to the skin. Without being bound by theory and to provide some further non-limiting examples, topical application may also be inhalational, such as asthma medications, or applied to the surface of tissues other than the skin, such as eye drops applied to the conjunctiva, or ear drops placed in the ear, or medications applied to the surface of a tooth. As a route of administration, topical administration is contrasted with enteral (in the digestive tract) and intravascular/intravenous (injected into the circulatory system). In its broadest sense, a topical effect may be understood in a way that it relates to, in the pharmacodynamic sense, a local, rather than systemic, target for a medication.

In a preferred embodiment, the anti-HSV antibody or the antigen-binding fragment thereof for use according to the present invention is a monoclonal or a polyclonal antibody. In a further preferred embodiment, the anti-HSV antibody or the antigen-binding fragment thereof for use according to the present invention is a humanized or a fully human antibody. In a further preferred embodiment, the anti-HSV antibody or the antigen-binding fragment thereof for use according to the present invention is a murine antibody.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies", refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant human antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "heterohybrid antibody" refers to an antibody having light and heavy chains of different organismal origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: JonesNature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins.

In a preferred embodiment, the anti-HSV antibody for use for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered, is a full-length antibody, i.e., to a full immunoglobulin molecule which is often also referred to as complete antibody.

"Single-chain Fv" or "scFv" antibody fragments have, in the context of the invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The antibody or fragment thereof as used in the context of the present invention for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered, is not particularly limited as long as it is an "anti-HSV antibody or an antigen-binding fragment thereof". Thus, the antibody may be any antibody which specifically binds to or specifically recognizes or interacts with a HSV, i.e., a domain, an antigen, preferably a surface-antigen of a HSV. The skilled person is readily in a position to generate such an antibody directed to a given domain (i.e., an antigen, preferably a surface-antigen of a HSV) and determine whether a respective antibody is capable of detecting/binding to a given domain, an antigen, preferably a surface-antigen of a HSV, preferably HSV-1 and/or HSV-2 based on the skilled person's common general knowledge and the methods described above.

In a preferred embodiment, the antibody of the invention binds to/recognizes the viral antigen glycoproteins D, B, C, H, L, E or I (i.e., gD, gB, gC, gH, gL, gE, gI) Glycoproteins D, B, C, H, L, E and I are surface or envelope proteins of HSV-1 and/or HSV-2. These proteins may not only be found on the surface or in the envelope structure of HSV-1 and/or HSV-2, i.e., on the surface of released infectious particles (i.e., the envelope of free virions) but they may also be present on the surface of infected cells, i.e., on the surface of cells. Yet, in a more preferred embodiment, the antibody of the invention binds to/recognizes the viral surface antigen glycoprotein D, B, C, H, L, E or I (i.e., gD, gB, gC, gH, gL, gE, or gI) of the HSV-1 and/or HSV-2 envelope. In a preferred embodiment, the anti-HSV antibody or the antigen-binding fragment thereof for use according to the present invention recognizes the surface glycoprotein B (gB) of the HSV-1 and/or HSV-2 envelope, preferably an epitope thereof. The glycoprotein B of HSV-1 and/or HSV-2 is well-characterized and, without being bound to specific sequences, examples sequences of various HSV-1 and HSV-2 strains, respectively, are shown in SEQ ID NOs:11 to 16. SEQ ID NO:11 shows the sequence of the glycoprotein B of HSV-1 strain F, SEQ ID NO:12 shows the sequence of the glycoprotein B of HSV-1 strain KOS, SEQ ID NO:13 shows the sequence of the glycoprotein B of HSV-1 strain gC-39-R6, SEQ ID NO:14 shows the sequence of the glycoprotein B of HSV-2 strain HG52, SEQ ID NO:15 shows the sequence of the glycoprotein B of HSV-2 strain 333 and SEQ ID NO:16 shows the sequence of the glycoprotein B of HSV-2 strain MMA. A sequence alignment of these glycoprotein B amino acid sequences shows that the overall amino acid homology of gB of HSV-1 and HSV-2 is 85% while the sequences are least conserved at the N- and C-terminal regions of the protein.

In a preferred embodiment, the anti-HSV antibody or the antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered, is capable of inhibiting the spreading of HSV from an infected cell to an adjacent second non-infected cell (cell-to-cell spread).

Cell-to-cell spread is the ability of the herpes virus to spread to an adjacent second non-infected cell without releasing cell-free particles. Reducing or eliminating the ability of the herpes virus to spread to an adjacent cell has the beneficial effect that the generation of lesions is avoided. In order to examine whether an antibody is capable of inhibiting the spread of HSV from an infected cell to an adjacent second non-infected cell (cell-to-cell spread), methods well-known to the person skilled in the art can be used. As an example, the following assay can be used: Vero cells grown to confluency on glass cover slips in 24-well tissue culture plates are infected for 4 h at 37° C. with a constant virus amount of 400 $TCID_{50}$/well. One median tissue culture infective dose (1 $TCID_{50}$) is the mount of a cytopathogenic agent, such as a virus, that will produce a cytopathic effect in 50% of the cell cultures inoculated. The virus inoculum is subsequently removed, the cells washed twice with PBS and further incubated for 2 days at 37° C. in 1 ml DMEM, 2% FCS, Pen/Strep containing an excess of either different anti-HSV antibodies or polyclonal anti-HSV control serum in order to prevent viral spreading via the supernatant. Viral antigens of HSV-infected cells are detected with a fluorescence labelled polyclonal goat-anti-HSV-serum (BETHYL Laboratories, Montgomery, Tex. USA, Catalog No. A190-136F, Lot No. A190-136F-2). Preferably, an antibody is inhibiting cell-to-cell spread if less than 20% of the adjacent cells are infected, preferably wherein less than 15%, less than 10%, less than 5%, more preferably less than 3% and most preferably less than 1% of the adjacent cells are infected in the above assay.

Cell-to-cell spread may also be assayed as follows: The presence of neutralizing antibodies does not necessarily prevent cell-to-cell spread of herpesviridae. To compare antibodies on disruption of HSV-1 and HSV-2 cell-to-cell spread this particular dissemination mode can be mimicked in vitro using standard test methods. E.g.: To infect individual cells, confluent Vero cell monolayers are initially incubated with either HSV-1 or HSV-2 at low MOI (e.g. 100 $TCID_{50}$), respectively. After 4 h of adsorption at 37° C., the viral inoculum has to be removed. To promote direct cell-to-cell transmission from individually infected cells but prevent viral spread through viral particles across the cell culture supernatant, Vero cell monolayers are treated with an excess of neutralizing anti-gB antibodies, controls, or medium alone. After 48 h virus spread can be detected by immunostaining with a mouse monoclonal antibody specific for a common epitope on glycoprotein D of HSV-1 and HSV-2 (e.g. Acris Antibodies, San Diego, Calif., USA) and fluorescence-conjugated secondary antibody. Immunofluorescence images can be acquired with a fluorescence microscope at a 100- or 400-fold magnification.

Moreover, in a preferred embodiment, the anti-HSV antibody of the present invention is capable of neutralizing HSV. "Neutralizing" herein means that the antibody opsonizes the virus so that it cannot infect any further cell. An assay for testing whether an antibody in a concentration of, e.g., at most 20 nM is capable of neutralizing a defined amount of HSV of, e.g., 100 $TCID_{50}$ Eis-Hübinger et al., Intervirology 32:351-360 (1991); Eis-Hübinger et al., Journal of General Virology 74:379-385 (1993) and in Examples 1 and 2 of WO2011/038933 A2. Thus, in a preferred embodiment, the antibody of the invention in a concentration of at most 20 nM, preferably of at most 16 nM, more preferably of at most 12 nM, such as of at most 10 nm, e.g., at most 8 nM or at most 6 nM, and most preferably of at most 4 nM is capable of neutralizing a defined amount of HSV of 100 $TCID_{50}$ to more than 80%, preferably by more than 90%, such as more than 95%, more preferably 96%, e.g., more than 97%, and most preferably more than 98%, e.g., more than 99% or even 100%.

Thus, in a preferred embodiment, the present invention also relates to an anti-HSV antibody or the antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered, wherein the antibody is capable of inhibiting cell-to-cell spread independent from antibody-dependent cellular cytotoxicity (ADCC) and/or complement-dependent cytotoxicity (CDC).

As the above-described assays for testing the capability whether an antibody is capable of inhibiting cell-to-cell spread do not contain complement and/or cytotoxic effector cells, the same assays may be used in order to determine whether an antibody is capable of inhibiting cell-to-cell spread independent from antibody-dependent cellular cytotoxicity (ADCC) and/or complement-dependent cytotoxicity (CDC).

In a preferred embodiment, the anti-HSV antibody or the antigen-binding fragment thereof for use according to the present invention comprises the complementarity determining regions $V_H$CDR1 comprising SEQ ID NO: 1, $V_H$CDR2 comprising SEQ ID NO: 2, $V_H$CDR3 comprising SEQ ID NO: 3, $V_L$CDR1 comprising SEQ ID NO: 4, $V_L$CDR2 comprising SEQ ID NO: 5, and $V_L$CDR3 comprising SEQ ID NO:6.

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the antibody molecule described herein above is selected from the group consisting of a full antibody (immunoglobulin, like an IgG1, an IgG2, an IgG2a, an IgG2b, an IgA1, an IgGA2, an IgG3, an IgG4, an IgA, an IgM, an IgD or an IgE), F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art, see e.g. (LoBuglio, Proceedings of the American Society of Clinical Oncology Abstract (1997), 1562 and Khor, Proceedings of the American Society of Clinical Oncology Abstract (1997), 847).

Accordingly, in the context of this invention, antibody molecules or antigen-binding fragments thereof are provided, which are humanized and can successfully be employed in pharmaceutical compositions.

Moreover, in a preferred embodiment, the antibody of the present invention is an antibody or antigen-binding fragment thereof that binds to the glycoprotein B (gB) of HSV-1 and/or HSV-2 which comprises or consists of VH domain (heavy chain variable region) and VL domain (light chain variable region), i.e., the amino acid sequence of the variable region of the heavy chain of an antibody as depicted in SEQ ID NO:9 and the amino acid sequence of the variable region of the light chain of an antibody as depicted in SEQ ID NO:10.

However, the antibody or antigen-binding fragment thereof as used in the present invention is not particularly limited to such variable heavy and light chain variable regions but may also be an antibody or antigen-binding fragment thereof that binds to the glycoprotein B (gB) of HSV-1 and/or HSV-2 envelope which comprises or consists of VH domain and VL domain with at least 95%, 90%, 85%, 75%, 70%, 65%, 60%, 55% or 50% sequence homology with the sequences of SEQ ID NOs: 9 and 10, respectively, as long as the antibody or antigen-binding fragment has the capability of having an effect in treating an acute infection of mucosal or epidermal tissue in a subject caused by HSV-1 or HSV-2 in terms of the present invention or being capable of inhibiting the spreading of HSV from an infected cell to an adjacent second non-infected cell (cell-to-cell spread) or being capable of inhibiting cell-to-cell spread independent from antibody-dependent cellular cytotoxicity (ADCC) and/or complement-dependent cytotoxicity (CDC) as described herein above and below. Furthermore, the antibody or antigen-binding fragment thereof is a molecule that comprises VH and VL domains having up to 0, 1, 2, 3, 4, 5, 6, 7, 8, 9, 10 or more conservative amino acid substitutions with reference to the sequences of SEQ ID NOs: 9 and 10. Moreover, the antibody or antigen-binding fragment thereof is an antibody fragment selected from the group consisting of Fab, Fab', Fab'-SH, FV, scFV, F(ab')2, and a diabody.

In order to determine whether an amino acid sequence has a certain degree of identity to the sequences of SEQ ID NOs: 9 and 10, the skilled person can use means and methods well known in the art, e.g. alignments, either manually or by using computer programs known to the person skilled in the art. Such an alignment can, e.g., be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences. In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity with the nucleic acid sequences or with the amino acid sequences as described above which are capable of binding to gB of HSV-1 or HSV-2 and having the capability of treating an acute infection of mucosal or epidermal tissue in a subject caused by HSV-1 or HSV-2 in terms of the present invention or being capable of inhibiting the spreading of HSV from an infected cell to an adjacent second non-infected cell (cell-to-cell spread) or being capable of inhibiting cell-to-cell spread independent from antibody-dependent cellular cytotoxicity (ADCC) and/or complement-dependent cytotoxicity (CDC) as described herein above and below), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably, the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff (1989) PNAS 89:10915) uses alignments (B) of 50, expectation (E) of 10, M=5, N=4, and a comparison of both strands.

Preferably, the amino acid substitution(s) are "conservative substitution(s)" which refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson Molecular Biology of the Gene, The Benjamin/Cummings Pub. Co. 4th Ed. (1987), 224. In addition, substitutions of structurally or functionally similar amino acids are less likely to disrupt biological activity. Within the context of the present invention the binding compounds/antibodies of the present invention comprise polypeptide chains with sequences that include up to 0 (no changes), 1, 2, 3, 4, 5, 6, 7, 8, 9, 10, 12, 15, 20 or more conservative amino acid substitutions when compared with the specific amino acid sequences disclosed herein, for example, SEQ ID NO: 9 (referring to the variable region of the antibody heavy chain of the antibody) and 10 (referring to the variable of the light chain of the antibody). As used herein, the phrase "up to X" conservative amino acid substitutions includes 0 substitutions and any number of substitutions up to 10 and including 0, 1, 2, 3, 4, 5, 6, 7, 8, 9, 10 substitutions.

Such exemplary substitutions are preferably made in accordance with those set forth in Table 1 as follows:

TABLE 1

Exemplary Conservative Amino Acid Substitutions

| Original residue | Conservative substitution |
| --- | --- |
| Ala (A) | Gly; Ser |
| Arg (R) | Lys; His |

TABLE 1-continued

Exemplary Conservative Amino Acid Substitutions

| Original residue | Conservative substitution |
| --- | --- |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Moreover, in a preferred embodiment, the anti-HSV antibody or the antigen-binding fragment thereof for use according to the present invention comprises an amino acid sequence with at least 70% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

In a further, preferred embodiment, the anti-HSV antibody or the antigen-binding fragment thereof for use according to the present invention comprises an amino acid sequence with at least 75%, at least 80%, more preferably at least 85%, at least 90%, even more preferably at least 95%, and most preferably 98% overall sequence identity in the framework regions compared to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8. Such antibodies are suitable for the medical uses of the present invention as long as the antibody or antigen-binding fragment binds to gB of HSV-1 or HSV-2 and has the capability of having an effect in treating an acute infection of mucosal or epidermal tissue in a subject caused by HSV-1 or HSV-2 in terms of the present invention or being capable of inhibiting the spreading of HSV from an infected cell to an adjacent second non-infected cell (cell-to-cell spread) or being capable of inhibiting cell-to-cell spread independent from antibody-dependent cellular cytotoxicity (ADCC) and/or complement-dependent cytotoxicity (CDC) as described herein above and below.

Thus, in a preferred embodiment, the anti-HSV antibody or the antigen-binding fragment thereof for use according to the present invention comprises an amino acid sequence having the above variable regions of the light and heavy chains (i.e., the CDRs defined above, i.e., $V_H$CDR1 comprising SEQ ID NO: 1, $V_H$CDR2 comprising SEQ ID NO: 2, $V_H$CDR3 comprising SEQ ID NO: 3, $V_L$CDR1 comprising SEQ ID NO: 4, $V_L$CDR2 comprising SEQ ID NO: 5, and $V_L$CDR3 comprising SEQ ID NO:6) while the amino acid sequence have a variability in the framework region with at least 75%, at least 80%, more preferably at least 85%, at least 90%, even more preferably at least 95%, and most preferably 98% overall sequence identity in the framework regions compared to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

In this context, a polypeptide has "at least X % sequence identity" in the framework regions to SEQ ID NO:7 or 8 if SEQ ID NO:7 or SEQ ID NO: 8 is aligned with the best matching sequence of a polypeptide of interest and the amino acid identity between those two aligned sequences is at least X % over positions 1 to 30, 38 to 51, 68 to 99, and 112 to 122 of SEQ ID NO: 7 and positions 1 to 23, 41 to 55, 63 to 94, and 104 to 114 of SEQ ID NO: 8. As mentioned above, such an alignment of amino acid sequences can be performed using, for example, publicly available computer homology programs such as the "BLAST" program provided on the National Centre for Biotechnology Information (NCBI) homepage using default settings provided therein. Further methods of calculating sequence identity percentages of sets of amino acid sequences or nucleic acid sequences are known in the art.

Moreover, in a preferred embodiment, the anti-HSV antibody or the antigen-binding fragment thereof for use according to the present invention comprises the $V_H$ of SEQ ID NO:9 and the $V_L$ of SEQ ID NO:10.

The specificity of the antibody or antigen-binding fragment of the present invention may not only be expressed by the nature of the amino acid sequence of the antibody or the antigen-binding fragment as defined above but also by the epitope to which the antibody is capable of binding to. Thus, the present invention utilizes in a preferred embodiment an anti-HSV antibody or an antigen-binding fragment thereof for use according to the present invention which recognizes the same epitope as the antibody as described above, preferably the mAbhu2c. As shown in the Examples section and as illustrated in FIGS. 13A and 13B of WO2011/038933 A2, this epitope is a discontinuous or rather a pseudocontinuous epitope partially resistant to denaturation located at the amino acids 172-195 and 295-313 of glycoprotein B of HSV-1 and HSV-2. In the context of the present application, the epitope of the mAb 2c antibody may be located within the first 487 amino-terminal residues of the gB protein. Preferably, the epitope may comprise at least one amino acid sequence located within the amino acid sequence between position 172 and 307 of the gB protein.

The epitope may comprise the consecutive amino acid sequence $_{301}YGYRE_{305}$ of the gB protein, preferably the consecutive amino acid sequence $_{301}YGYREG_{306}$ or $_{300}FYGYRE_{305}$, more preferably the sequence may be further extended at the termini (i.e., $_{299}PFYGYRE_{305}$ or $_{300}FYGYREGS_{307}$). The epitope of the antibodies of the present invention may comprise the consecutive amino acid sequence 298-313 ($_{298}SPFYGYREGSHTEHTS_{313}$) of gB.

Alternatively, the epitope may be located in the consecutive amino acid sequence $_{172}QVWFGHRYSQFM$-$GIFED_{188}$. The epitope may comprise the consecutive amino acid sequence $_{172}QVWFGHRYSQFMG_{184}$.

Preferably, the epitope may be consisted of more than one consecutive amino acid sequences. The epitope may partly be a discontinuous epitope. More preferably, the epitope may comprise two consecutive amino acid sequences. Such an epitope consisting of two amino acid sequences may be designated as "duotope". The antibody may bind to both amino acid sequences.

More preferably, the amino acid sequences of the duotope may comprise the amino acid sequence $_{300}FYGYRE_{305}$ and an amino acid sequence located between amino acid position 172 and 188. Even more preferably, the epitope may comprise the amino acid sequence $_{300}FYGYRE_{305}$ and amino acid sequence $_{179}YSQFMG_{184}$ of the gB protein. Alternatively, the epitope or the duotope may be chemically synthesized. The epitope may be a chemically synthesized epitope having the sequence YSQFMG-βA-FYGYRE. The abbreviation βA as used herein refers to beta-alanine.

Most preferably, the epitope may comprise the amino acid sequence FYGYRE and amino acid sequence FED of the gB protein. The epitope may be a chemically synthesized epitope having the sequence FED-βA-βA-FYGYRE or PFYGYREGFEDF.

It may be understood by a person skilled in the art that the epitopes may be comprised in the gB protein, but may also be comprised in a degradation product thereof or may be a chemically synthesized peptide. The amino acid positions are only indicated to demonstrate the position of the corresponding amino acid sequence in the sequence of the gB protein. The invention encompasses all peptides comprising the epitope. The peptide may be a part of a polypetide of more than 100 amino acids in length or may be a small peptide of less than 100, preferably less than 50, more preferably less than 25 amino acids, even more preferably less than 16 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophor), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane.

In order to test whether an antibody in question and the antibody of the present invention recognize the same epitope, the following competition study may be carried out: Vero cells infected with 3 moi (multiplicity of infection) are incubated after 20 h with varying concentrations of the antibody in question as the competitor for 1 hour. In a second incubation step, the antibody of the present invention is applied in a constant concentration of 100 nM and its binding is flow-cytometrically detected using a fluorescence-labelled antibody directed against the constant domains of the antibody of the invention. Binding that conducts anti-proportional to the concentration of the antibody in question is indicative for that both antibodies recognize the same epitope. However, many other assays are known in the art which may be used.

Thus, in a preferred embodiment, the anti-HSV antibody or the antigen-binding fragment thereof for use according to the present invention recognizes the same epitope as mAb 2c, wherein said epitope is located at the amino acids 172-195 and 295-315 of glycoprotein B of HSV-1 and HSV-2. Using overlapping 15-mer peptides spanning the gB region from amino acid 31 to 505 it has been described in Daumer et al., Med Microbiol Immunol 2011 (200):85-97 that the mAb 2c is capable of recognizing an epitope which is located at the amino acids 175-195 and 298-315 of glycoprotein B of HSV-1 and HSV-2. Using high-resolution 13-mer peptide microarrays Krawczyk et al., Journal of Virology 2011 (85):1793-1803 mapped the epitope recognized by mAb 2c to the amino acids 172-195 and 295-313 of glycoprotein B of HSV-1 and HSV-2.

The sequence of the glycoprotein B of HSV-1 and/or HSV-2 is well-characterized and, as defined above, without being bound to specific sequences, examples sequences of various HSV-1 and HSV-2 strains, respectively, are shown in SEQ ID NOs:11 to 16. The epitope recognized by the mAb 2c antibody is highly conserved among various HSV-strains as well as between HSV-1 and HSV-2.

This antibody or the antigen-binding fragment thereof which may be used in the treatment as disclosed in the present invention is not limited to the antibody detecting the above epitope of glycoprotein B of HSV-1 and HSV-2. In fact, also other antibodies which detect another epitope of glycoprotein B or even an epitope of another protein or polypeptide of HSV-1 and HSV-2 can be used in the treatment of the present invention as long as such an antibody is capable of having an effect in treating an acute infection of mucosal or epidermal tissue in a subject caused by HSV-1 or HSV-2 in terms of the present invention or being capable of inhibiting the spreading of HSV from an infected cell to an adjacent second non-infected cell (cell-to-cell spread) or being capable of inhibiting cell-to-cell spread independent from antibody-dependent cellular cytotoxicity (ADCC) and/or complement-dependent cytotoxicity (CDC) as described herein above and below.

With the normal skill of the person skilled in the art and by routine methods, the person skilled in the art can easily deduce from the sequences provided herein relevant epitopes (also functional fragments) of the polypeptides of HSV which are useful in the generation of antibodies like polyclonal and monoclonal antibodies. However, the person skilled in the art is readily in a position to also provide for engineered antibodies like CDR-grafted antibodies or also humanized and fully human antibodies and the like.

Particularly preferred in the context of the present invention are monoclonal antibodies. For the preparation of monoclonal antibodies, any technique which provides antibodies produced by continuous cell line cultures can be used. Examples for such techniques include the hybridoma technique, the trioma technique, the human B-cell hybridoma technique and the EBV-hybridoma technique to produce human monoclonal antibodies (Shepherd and Dean (2000), Monoclonal Antibodies: A Practical Approach, Oxford University Press, Goding and Goding (1996), Monoclonal Antibodies: Principles and Practice—Production and Application of Monoclonal Antibodies in Cell Biology, Biochemistry and Immunology, Academic Pr Inc, USA).

The antibody derivatives can also be produced by peptidomimetics. Further, techniques described for the production of single chain antibodies (see, inter alia, U.S. Pat. No. 4,946,778) can be adapted to produce single chain antibodies specifically recognizing an antigen of HSV. Also, transgenic animals may be used to express humanized antibodies to the polypeptide of HSV.

The present invention also envisages the production of specific antibodies against native polypeptides and recombinant polypeptides of glycoprotein B or any another protein or polypeptide of HSV-1 and HSV-2. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of HSV-1 or HSV-2 can be subcloned into an appropriated vector, wherein the recombinant polypeptide is to be expressed in an organism being able for an expression, for example in bacteria. Thus, the expressed recombinant protein can be intra-peritoneally injected into a mice and the resulting specific antibody can be, for example, obtained from the mice serum being provided by intra-cardiac blood puncture. The present invention also envisages the production of specific antibodies against native polypeptides and recombinant polypeptides by using a DNA vaccine strategy as exemplified in the appended examples. DNA vaccine strategies are well-known in the art and encompass liposome-mediated delivery, by gene gun or jet injection and intramuscular or intradermal injection. Thus, antibodies directed against a polypeptide or a protein or an epitope of HSV-1 and HSV-2 can be obtained by directly immunizing the animal by directly injecting intramuscularly the vector expressing the desired polypeptide or a protein or an epitope of HSV-1 and HSV-2, in particular an epitope of gB. The amount of obtained specific antibody can be quantified using an ELISA, which is also described herein below. Further methods for the production of antibodies are well known in the art, see, e.g. Harlow and Lane, "Antibodies, A Laboratory Manual", CSH Press, Cold Spring Harbor, 1988. The term "specifically binds", as used herein, refers to a binding reaction that is determinative of the presence of the desired polypeptide or a protein or an epitope of HSV-1 and HSV-2, in particular an epitope of gB, and an antibody in the presence of a heterogeneous population of proteins and other biologics.

Thus, under designated assay conditions, the specified antibodies and a corresponding polypeptide or a protein or an epitope of HSV-1 and HSV-2, in particular an epitope of gB, bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Shepherd and Dean (2000), Monoclonal Antibodies: A Practical Approach, Oxford University Press and/or Howard and Bethell (2000) Basic Methods in Antibody Production and Characterization, Crc. Pr. Inc. for a description of immunoassay formats and conditions that can be used to determine specific immunoreactivity. Typically a specific or selective reaction will be at least twice background signal to noise and more typically more than 10 to 100 times greater than background. The person skilled in the art is in a position to provide for and generate specific binding molecules directed against the novel polypeptides. For specific binding-assays it can be readily employed to avoid undesired cross-reactivity, for example polyclonal antibodies can easily be purified and selected by known methods (see Shepherd and Dean, loc. cit.).

The term "anti-HSV antibody or antigen-binding fragment thereof" means in accordance with this invention that the antibody molecule or antigen-binding fragment thereof is capable of specifically recognizing or specifically interacting with and/or binding to at least two amino acids of the desired polypeptide or a protein or an epitope of HSV-1 and HSV-2, in particular an epitope of gB. Said term relates to the specificity of the antibody molecule, i.e. to its ability to discriminate between the specific regions a desired polypeptide or a protein or an epitope of HSV-1 and HSV-2, in particular an epitope of gB. Accordingly, specificity can be determined experimentally by methods known in the art and methods as disclosed and described herein. Such methods comprise, but are not limited to Western blots, ELISA-, RIA-, ECL-, IRMA-tests and peptide scans. Such methods also comprise the determination of $K_D$-values as, inter alia, illustrated in the appended examples. The peptide scan (pepspot assay) is used routinely employed to map linear epitopes in a polypeptide antigen. The primary sequence of the polypeptide is synthesized successively on activated cellulose with peptides overlapping one another. The recognition of certain peptides by the antibody to be tested for its ability to detect or recognize a specific antigen/epitope is scored by routine colour development (secondary antibody with horseradish peroxide and 4-chloronaphtol and hydrogenperoxide), by a chemoluminescence reaction or similar means known in the art. In the case of, inter alia, chemoluminescence reactions, the reaction can be quantified. If the antibody reacts with a certain set of overlapping peptides one can deduce the minimum sequence of amino acids that are necessary for reaction. The same assay can reveal two distant clusters of reactive peptides, which indicate the recognition of a discontinuous, i.e. conformational epitope in the antigenic polypeptide (Geysen (1986), Mol. Immunol. 23, 709-715).

A preferred epitope of the anti-HSV antibody or antigen-binding fragment thereof is defined above and below is the same that is recognized by the mAb2c.

In a preferred embodiment, the anti-HSV antibody (or an antigen-binding fragment thereof) for use according to the present invention is the mAb 2c antibody (or an antigen-binding fragment thereof). This monoclonal antibody MAb 2c has been described elsewhere and has been demonstrated to neutralize virus by abrogating viral cell-to-cell spread, a key mechanism by which HSV-1/2 escapes humoral immune surveillance independent from antibody-dependent cellular cytotoxicity (ADCC) and/or complement-dependent cytotoxicity (CDC); Eis-Hübinger et al., Intervirology 32:351-360 (1991); Eis-Hübinger et al., Journal of General Virology 74:379-385 (1993); WO2011/038933 A2; Krawczyk A, et al., Journal of virology (2011); 85(4):1793-1803; Krawczyk A, et al., Proc Natl Acad Sci USA (2013); 110(17):6760-6765.

The antibodies and antigen-binding-fragments thereof as defined above are particularly useful in medical settings involving the topical administration. Thus, as mentioned above, the present invention relates to the medical use of an anti-HSV antibody or antigen-binding fragment thereof wherein said antibody or antigen-binding fragment thereof is topically administered. Accordingly, the present invention relates to an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said antibody is to be topically administered.

The term "treatment" and the like are used herein to generally mean obtaining a desired pharmacological and/or physiological effect. As already described above, the treatment of the present invention relates to the treatment of acute infections and, accordingly, excludes that the effect may be prophylactic in terms of completely or partially preventing a disease or symptom thereof. Rather, the term "treatment" is to be understood as being therapeutic in terms of partially or completely curing a disease and/or adverse effect and/or symptoms attributed to the disease of an acute HSV infection as defined above. Hence, the treatment of the present invention relates to the treatment of acute infections. "Acute" in this respect means that the subject shows symptoms of the disease. In other words, the subject to be treated is in actual need of a treatment and the term "acute treatment" in the context of the present invention relates to the measures taken to actually treat the disease after the onset of the disease or the breakout of the disease. The term "acute" as referred to in the context of the present invention is opposed to a prophylactic treatment or preventive treatment, i.e., measures taken for disease prevention, e.g., in order to prevent the infection and/or the onset of the disease. More specifically, prophylactic treatment may be understood in a way that it prevents attachment of free virus particles (from outside the body) to target cells and in turn prevents virus replication. In contrast, at an acute infection (which could be a primary or a recurrent infection) progeny virus have been raced upon HSV replication. Thus, the "acute treatment" referred to in the present invention does explicitly not relate to prophylactic or preventive treatment of an infection caused by HSV-1 or HSV-2.

Topical administration in accordance with the present invention relates to a medication or application or administration that is applied to body surfaces such as the skin or mucous membranes to treat the infection referred to above via a large range of classes of forms of administration, including but not limited to creams, foams, gels, lotions and ointments. In a preferred embodiment, topical administration is understood to be epicutaneous, meaning that the anti-HSV antibody or an antigen-binding fragment thereof is applied directly to the skin. Without being bound by theory and to provide some further non-limiting examples, topical application may also be inhalational, such as asthma medications, or applied to the surface of tissues other than the skin, such as eye drops applied to the conjunctiva, or ear drops placed in the ear, or medications applied to the surface of a tooth. As a route of administration, topical administration are contrasted with enteral (in the digestive tract) and intravascular/intravenous (injected into the circulatory system). In its broadest sense, a topical effect may be understood in a way that it relates to, in the pharmacodynamic sense, a local, rather than systemic, target for a medication.

The mode of topical administration in accordance with the present invention, i.e., the medication, pharmaceutical composition or application or administration that is applied to body surfaces such as the skin or mucous membranes to treat the infection of acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum is not particularly limited and the skilled person knows many forms and preparations that may be suitable for topical administration. Without being bound by theory and without being limiting, the following examples are given. There are many general classes, with no clear dividing line between similar formulations suitable for topical medication. As an example, a topical solution may be used. Topical solutions are generally of low viscosity and often use water or alcohol in the base.

As another example, a lotion may be used to administer the anti-HSV antibody topically. Lotions are similar to solutions but are thicker and tend to be more emollient in nature than solution. They are usually an oil mixed with water, and more often than not have less alcohol than solutions.

As another example, a cream may be used to administer the anti-HSV antibody topically. A cream is usually an emulsion of oil and water in approximately equal proportions. It penetrates the stratum corneum outer layer of skin well. Cream is thicker than lotion, and maintains its shape when removed from its container. It tends to be moderate in moisturizing tendency.

As another example, an ointment may be used to administer the anti-HSV antibody topically. An ointment is commonly a homogeneous, viscous, semi-solid preparation, most commonly a greasy, thick oil (oil 80%-water 20%) with a high viscosity, that is intended for external application to the skin or mucous membranes. Ointments have a Water number that defines the maximum amount of water that it can contain. They may be used as emollients or for the application of the anti-HSV antibody in accordance with the present invention to the skin for protective, therapeutic, or prophylactic purposes and where a degree of occlusion is desired. The vehicle of an ointment is known as the ointment base. The choice of a base depends upon the clinical indication for the ointment and is appropriately chosen based on the person skilled in the art's knowledge. Different types of ointment bases may be hydrocarbon bases, e.g. hard paraffin, soft paraffin, microcrystalline wax and ceresine; absorption bases, e.g. wool fat, beeswax; water soluble bases, e.g. macrogols 200, 300, 400; emulsifying bases, e.g. emulsifying wax, cetrimide; vegetable oils, e.g. olive oil, coconut oil, sesame oil, almond oil and peanut oil. Commonly, the medicament, i.e., the anti-HSV antibody in the present invention, is dispersed in the base, and later they get divided after the drug penetration into the living cells of skin. Ointments are commonly formulated using hydrophobic, hydrophilic, or water-emulsifying bases to provide preparations that are immiscible, miscible, or emulsifiable with skin secretions. They can also be derived from hydrocarbon (fatty), absorption, water-removable, or water-soluble bases.

As another example, a gel may be used to administer the anti-HSV antibody topically. Gels are usually thicker than a solution. Gels are often a semisolid emulsion in an alcohol base. Some will melt at body temperature. Gel tends to be cellulose cut with alcohol or acetone.

As another example, a foam may be used to administer the anti-HSV antibody topically.

As another example, a transdermal patch may be used to administer the anti-HSV antibody topically. Transdermal patches can be a very precise time released method of delivering a drug. The release of the active component from a transdermal delivery system (patch) may be controlled by diffusion through the adhesive which covers the whole patch, by diffusion through a membrane which may only have adhesive on the patch rim or drug release may be controlled by release from a polymer matrix. As another example, a powder may be used to administer the anti-HSV antibody topically. Powder is either the pure drug by itself (talcum powder), or is made of the drug mixed in a carrier such as corn starch or corn cob powder (Zeosorb AF—miconazole powder).

As another example, a solid form may be used to administer the anti-HSV antibody topically. Thus, the anti-HSV antibody may be placed in a solid form. Examples are deodorant, antiperspirants, astringents, and hemostatic agents. In a preferred embodiment, in particular in the context of the topical administration of the anti-HSV antibody in the treatment of an acute infection of mucosal or epidermal tissue caused by HSV-1 or HSV-2 of Herpes simplex genitalis, the anti-HSV antibody may be administered in the form of a suppository. A suppository is a drug delivery system that in the context of the treatment of Herpes simplex genitalis comprises the anti-HSV antibody and may be is inserted into the vagina (i.e., in the form of a vaginal suppository), where it dissolves or melts and releases the anti-HSV antibody and, accordingly serves to deliver locally the anti-HSV-antibody.

As another example, a vaporizing device may be used to administer the anti-HSV antibody topically. Thus, the anti-HSV antibody may be applied as an ointment or gel, and reach the mucous membrane via vaporization.

As another example, a paste may be used to administer the anti-HSV antibody topically. Paste combines three agents—oil, water, and powder. It is an ointment in which a powder is suspended.

As a final, non-limiting example, a tincture may be used to administer the anti-HSV antibody topically. A tincture is a skin preparation that has a high percentage of alcohol.

In another embodiment, the anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, is to be topically applied to infected mucosal or epidermal tissue. The area the anti-HSV antibody or an antigen-binding fragment thereof is to be applied to is not particularly limited. Preferably, an area of the mucosal or epidermal tissue is chosen which displays acute symptoms of an infection caused by HSV-1 or HSV-2. Preferably, these areas or parts of the subject's body are the lips, genitals, nose, ears, eyes, fingers, toes and/or skin areas throughout the body, preferably on the head, the jaw area, neck, chest, face, stomach and/or legs. In particular, in cutaneaous Herpes simplex infection as described above, commonly (larger) skin areas throughout the body can be affected while in Herpes gladiatorum as described above, it usually occurs on the head, most commonly the jaw area, the neck, chest, face, stomach, and legs. Accordingly, in these diseases, it is preferred that the topical administration in accordance with the invention is effected to these body parts or areas of mucosal or epidermal tissue.

In a further preferred embodiment, the anti-HSV antibody or the antigen-binding fragment thereof for use in accordance with the present invention is to be topically applied to areas surrounding the infected mucosal or epidermal tissue. Areas surrounding the infected mucosal or epidermal tissue are to be understood as the area around a given infected location of the tissue. The extent of the area of the surrounding is not particularly limiting but may cover, e.g., an area adjacent to/surrounding the infected tissue which has approximately 0.5 times the size of the infected area, the same size of the infected area, 1.5 times, preferably 2 times or even more preferably 3, 4 or 5 times the size of the infected area.

The anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said anti-HSV antibody or an antigen-binding fragment thereof is to be topically applied may be administered in combination with a virostatic agent. Preferably, such a combination therapy exerts synergistic effects on the treatment in accordance with the present invention.

The term "combination" as used herein relates to a combination of anti-HSV antibody or an antigen-binding fragment thereof as outlined above and a virostatic agent described herein below. In a preferred embodiment, a simultaneous application is envisaged. Yet, the combination also encompasses a subsequent application of the two components, i.e. anti-HSV antibody or an antigen-binding fragment thereof as outlined above and a virostatic agent described herein below. Thus, one of these components may be administered before, simultaneously with or after the other one of the combination, or vice versa. Accordingly, "in combination" as used herein does not restrict the timing between the administration of the anti-HSV antibody or an antigen-binding fragment thereof as outlined above and a virostatic agent described herein below. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

Virostatic agents are well-known to the person skilled in the art and are commonly also referred to as antiviral drugs which are a class of medication used specifically for treating viral infections. Specific antivirals are used for specific viruses. Unlike most antibiotics, antiviral drugs do not destroy their target pathogen; instead they inhibit their development.

With respect to HSV infections, the skilled person is in a position to select an appropriate virostatic agent that is suitable to inhibit the virus' development in accordance with the present invention. As examples, virostatic agent may be selected from the group consisting of the drug classes of nucleoside analogues, pyrophosphate analogues, nucleotide analogues, amantadin derivatives and helicase-primase inhibitors. Thus, the present invention relates to an anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum, wherein said anti-HSV antibody or an antigen-binding fragment thereof is to be topically applied in combination with a virostatic agent selected from the group consisting of the drug classes of nucleoside analogues, pyrophosphate analogues, nucleotide analogues, and helicase-primase inhibitors.

Nucleoside analogues are known in the art and relate to molecules that act like nucleosides in DNA synthesis. They include a range of antiviral products used to prevent viral replication in infected cells. Once they are phosphorylated, they work as antimetabolites by being similar enough to nucleotides to be incorporated into growing DNA strands, but they act as chain terminators and stop viral DNA Polymerase. Nucleoside, nucleotide and pyrophosphate analogues in general are known to inhibit viral nucleic acid synthesis to block viral replication. Nucleoside, nucleotide analogues are antimetabolite drugs. Pyrophosphate analogues (e.g. Foscarnet) structurally mimic the anion pyrophosphate and exert antiviral activity by a selective inhibition of the pyrophosphate binding site on virus-specific DNA polymerases at concentrations that do not affect cellular DNA polymerases. Nucleotide and pyrophosphate analogues do not require an initial activation (phosphorylation) by thymidine kinases or other kinases before taken up into cells. Helicase-primase inhibitors are non-nucleosidic inhibitors that target the viral helicase-primase.

Preferably, commonly known and approved virostatic agents may be used as summarized in the following. As a nucleoside analogue a compound selected from the group consisting of Acyclovir, Penciclovir, Valacyclovir and Famaciclovir may exemplarily be mentioned and used in the combination therapy described above. As a pyrophosphate analogue Foscarnet may be used. As a nucleotide analogue Cidofovir may be used. As a helicase-primase inhibitor Pritelivir is exemplarily mentioned. As an amantadine derivative, Tromantandin may be used.

Acyclovir, also known as acycloguanosine (ACV) or 2-Amino-9-(2-hydroxyethoxymethyl)-3H-purin-6-on, is a guanosine analogue antiviral drug, marketed under trade names such as, ACERPES®, Acic®, Aciclobeta®, AcicloCT®, Aciclostad®, Aciclovir, Acic®, Ophtal®, Acivir®, AciVision, Acyclovir®, Aviral®, Cyclovir, Helvevir®, Herpex, Supraviran®, Virucalm®, Virupos® Virzin, Zoliparin®, Zovir, and Zovirax®.

Penciclovir (2-amino-9-[4-hydroxy-3-(hydroxymethyl) butyl]-6,9-dihydro-3H-purin-6-on) is a guanine analogue antiviral drug, marketed under trade names such as Denavir and Fenistil.

Famciclovir (2-[(acetyloxy)methyl]-4-(2-amino-9H-purin-9-yl)butyl acetate) is a prodrug of penciclovir with improved oral bioavailability.

Foscarnet is the conjugate base of the chemical compound with the formula $HO_2CPO_3H_2$ and is marketed under the trade names Foscavir® and Triapten®. Valacyclovir, also known as (S)-2-[(2-amino-6-oxo-6,9-dihydro-3H-purin-9-yl)methoxy]ethyl-2-amino-3-methylbutanoate, is a prodrug of the guanosine analogue antiviral drug ACV marketed under the name e.g. Valtrex®.

Cidovovir (CDV), also known as (S)-1-[3-hydroxy-2-(phosphonylmethoxypropyl)cytosine, is a nucleotide analogue antiviral drug marketed under the name Visitde®.

Pritelevir is a thiazolylamide, also known as AIC-316, or BAY 57-1293, is a helicase-primase inhibitor currently in clinical phase II trials for treatment of genital HSV-2 infections.

The local therapeutic drug Tromantandin (Viru-Merz Serol Gel) is explicitly used for local treatment of HSV skin infections. Tromantandin is an amantadin derivative. Griffin U.S. Pat. No. 4,351,847 discloses that an amantadine derivative is effective against herpes simplex virus.

Moreover, the present invention relates to a pharmaceutical composition, comprising an effective amount of the antibody or the antigen-binding fragment thereof in accordance with the above and at least one pharmaceutically acceptable excipient.

An excipient is an inactive substance formulated alongside the active ingredient, i.e., the anti-HSV antibody or the antigen-binding fragment thereof in accordance with the above, for the purpose of bulking-up formulations that contain potent active ingredients. Excipients are often referred to as "bulking agents," "fillers," or "diluents". Bulking up allows convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

Thus, in line with the above, the pharmaceutical composition comprising an effective amount of the antibody or the antigen-binding fragment thereof may be in solid, liquid or gaseous form and may be, inter alia, in a form of (a) powder(s), (a) tablet(s), (a) solution(s) or (an) aerosol(s). It is preferred that said pharmaceutical composition optionally comprises a pharmaceutically acceptable carrier and/or diluent.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e., in "an effective amount" which can easily be determined by the skilled person by methods known in the art. Administration of the suitable pharmaceutical composition is effected in accordance with the present invention by topical administration. The dosage regimen will be determined by the attending physician and clinical factors. As is well known in the medical arts, dosages for any one patient depends upon many factors, including the patient's or subject's size, body surface area, age, the particular compound to be administered, sex, time and route of administration, general health, and other drugs being administered concurrently. Proteinaceous pharmaceutically active matter may be present in amounts between 0.1-10 µg/kg body weight per dose; however, doses below or above this exemplary range are envisioned, especially considering the aforementioned factors. For topical administration as it is particularly preferred in the context of the present invention, a pharmaceutically active matter suitable for topical administration as defined herein further above and below containing antibody concentrations of 0.1 to 10 mg/ml, preferably of 0.5 to 5 mg/ml is particularly envisaged. This corresponds to the ranges used in the Examples as exemplified further below wherein the antibody in liquid solution (PBS) or mixed 1:2 with créme at concentrations between 0.5 to 5 mg/ml has been used which corresponds to 0.5 to 5 mg/g in PBS or a créme with the same density of PBS.

Thus, preferably, the antibody or the antigen-binding fragment thereof and/or the virostatic agent are included in an effective amount. The term "effective amount" refers to an amount sufficient to induce a detectable therapeutic response in the subject to which the pharmaceutical composition is to be administered. In accordance with the above, the content of the antibody in the pharmaceutical composition is not limited as far as it is useful for treatment as described above, but preferably contains 0.0000001-10% by weight per total composition. Further, the antibody described herein is preferably employed in a carrier. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilisers are non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

Progress can be monitored by periodic assessment. The antibody, antigen-binding fragment thereof or the pharmaceutical composition of the invention are administered locally as defined above in contrast to a systemic administration. Preparations for topical administration have already been described above and include, inter alia, sterile aqueous or non-aqueous solutions, suspensions, and emulsions as well as creams and suppositories. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be, e.g., Tween, EDTA, Citrate, Sucrose as well as other agents being suitable for the intended use of the pharmaceutical composition that are well-known to the person skilled in the art.

In accordance with this invention, the term "pharmaceutical composition" relates to a composition for administration to a patient, preferably a human patient. In the context of the present invention that medicament/pharmaceutical composition is to be administered topically to a patient who suffers from an acute infection of mucosal or epidermal tissue caused by HSV-1 or HSV-2 in accordance with the present invention. In the context of the present invention, the subject, i.e., the patient refers to human patient. Thus, the present invention also relates to a pharmaceutical composition, comprising an effective amount of the antibody or the antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum and at least one pharmaceutically acceptable excipient. As regards the preferred embodiments of the pharmaceutical composition the same applies, mutatis mutandis, as has been set forth above in the context of the anti-HSV antibody or an antigen-binding fragment thereof for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum wherein said antibody is to be topically administered as well as the pharmaceutical composition as defined above.

The invention also relates to a method for the treatment of an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum comprising the step of topically administering the antibody or antigen-binding fragment as defined above. Thus, the present invention relates to a method of the treatment of acute infections of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum in a subject wherein the antibody or the antigen-binding fragment thereof is administered topically to the subject in a therapeutically effective amount. As regards the preferred embodiments of the method for treatment the same applies, mutatis mutandis, as has been set forth above in the context of the anti-HSV antibody or an antigen-binding fragment thereof or the pharmaceutical composition for use in treating an acute infection of mucosal or epidermal tissue in a subject caused by HSV-1 or HSV-2 selected from the group consisting of Herpes simplex labialis, Herpes simplex genitalis, chronic or disseminated cutaneous herpes simplex infection, Herpes gladiatorum and Eczema herpeticum wherein said antibody is to be topically administered as well as the pharmaceutical composition as defined above.

In the present invention, the subject is in a preferred embodiment a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

Other aspects and advantages of the invention will be described in the following examples, which are given for purposes of illustration and not by way of limitation. Each publication, patent, patent application or other document cited in this application is hereby incorporated by reference in its entirety.

FIG. 1: compares the survival of immunodeficient mice with acute genital HSV-2 infection after topical treatment either with the humanized monoclonal antibody hu2c or acyclovir. Female mice (NOD.CB17-Prkdc$^{scid}$/NCrHsd) were treated with a long-acting progestin (Depo-Clinovir, Pharmacia) 7 days prior to viral challenge to increase susceptibility to HSV-2 infection and to eliminate differences caused by the estrous cycle. Anesthetized mice were vaginally challenged with a lethal dose of $5\times10^5$ PFU of HSV-2 G (20 µl). Mice displaying visible infection (perineal hair loss, reddening, swelling) were treated one day after viral challenge (A) once with 40 µl hu2c (5 mg/ml) (●) or 40 µl control IgG (5 mg/ml) (□) or (B) twice daily for 4 days with 40 µl ACV (25 mg/ml) (Δ) or 40 µl PBS (x). Drug solutions or PBS were applied topically to the outer genital epithelium. Mice were monitored for 36 days after viral inoculation. Mice displaying sever systemic signs and/or severe lesions/zoster were killed. Surviving mice were sacrificed at day 36. Test groups contained eight animals each, control groups contained five animals each. Kaplan-Meier survival curves were analyzed by log-rank (Mantel-Cox) test. Two-tailed significance tests were used to compare the significance level between two groups. All protocols were approved by the Animal Care and Use Committee.

Figure 2:
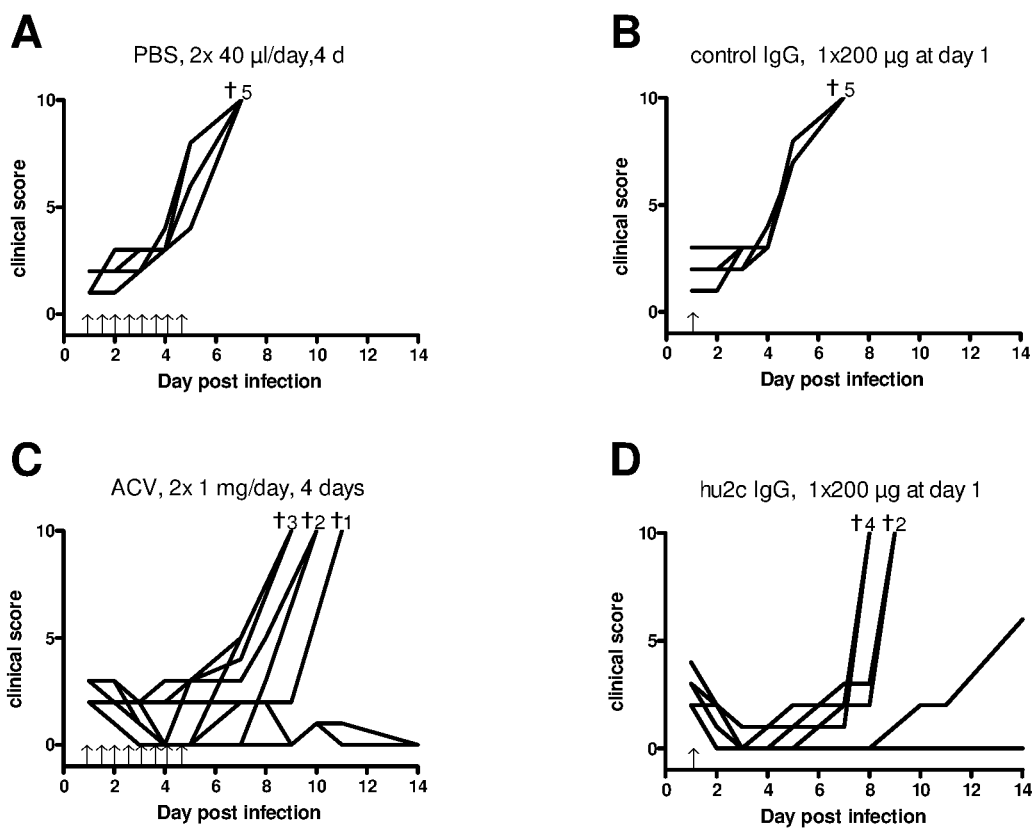

FIG. 2: shows the clinical scoring of acute genital HSV-2 infection after topical treatment with the humanized monoclonal antibody hu2c or acyclovir. Mice displaying visible infection (perineal hair loss, reddening, swelling) one day after intravaginal challenge with a lethal dose of $5\times10^5$ PFU of HSV-2 G (20 µl) were treated (A & C) twice daily for 4 days with (A) 40 µl PBS or (C) 40 µl ACV (25 mg/ml), or treated (B & D) once at 24 h post infection with (B) 40 µl hu2c (5 mg/ml) or (D) 40 µl control IgG (5 mg/ml). Drug solutions or PBS were applied topically to the outer genital epithelium.

Infected animals were observed daily and their clinical status was scored as follows: 0, lack of symptoms, no lesions; 1-2, redness and/or swelling (erosion); 3, localized lesion <1 mm; 4-5, localized lesion 2-3 mm; 6-7 localized lesion 4-5 mm; 8-9, severe hyperemia, destruction of the epithelium and stroma with necrosis; 10, systemic signs, death. Animals with grading >8 were killed to prevent undue suffering. Test groups contained eight animals each, control groups contained five animals each. Arrows indicate time points of treatment.

EXAMPLES

Example 1: Topical Application of a Humanized Anti-HSV Antibody

1. Subjects, Materials, Methods
1.1 Generation and Production of a HSV Neutralizing Humanized Monoclonal Antibody.

Recently, it has been demonstrated that cross-linking of a highly conserved glycoprotein B epitope of HSV-1/2 through the murine monoclonal antibody mAb 2c does not only result in highly efficient neutralization of free virions but also in inhibition of direct virus spread from infected to non-infected cells (Krawczyk A, et al., Journal of virology 2011; 85(4):1793-1803). To exploit these unique properties for therapeutic use in humans, we generated a humanized derivative of mAb 2c.

For the vast majority of humanized antibodies retention of a set of potentially immunogenic murine residues within the human frameworks is usually required for maintaining the structural integrity of the grafted antigen binding loops. In order to generate a humanized antibody with the lowest possible immunogenic potential any framework manipulations had been avoided by careful selection of appropriate human germline sequences and simultaneous employment of our previously described sequence multi-alignment approach (Krauss J, et al., *Protein Eng* 2003; 16(10):753-759).

To identify appropriate human germline acceptor scaffolds for grafting the mAb 2c complementarity determining regions (CDRs), variable domain framework sequences of mAb 2c were aligned to corresponding human sequences of the V Base database (http://vbase.mrc-cpe.cam.ac.uk/). The highest framework sequence identities to the corresponding murine mAb 2c variable light ($V_L$) and variable heavy ($V_H$) chain sequence showed the human germline sequences DP28 (88.5%) and DPK13 (88.9%), respectively. Hence, CDR coding gene segments of the murine donor-antibody 2c (i.e. 2c $V_L$-CDR1/2/3 and 2c $V_H$-CDR1/2/3) were grafted into acceptor frameworks coding for DP28 and DPK13, respectively. Variable domain encoding genes of the chimeric and humanized $V_L$ chain and $V_H$ chain were subsequently cloned into immunoglobulin expression vectors containing a human constant heavy γ1 chain, and a human constant κ chain, respectively. The humanized antibody was either produced from stably transfected Sp2/0 mouse myeloma cell lines or transient transfected HEK293 cells under serum-free conditions and purified from culture supernatants to homogeneity by protein A chromatography. Purity was assessed by gel filtration chromatography (Superdex 200GL, GE Healthcare) as ≥95% (Krawczyk A, et al., Proc Natl Acad Sci USA 2013; 110(17):6760-6765).

1.2 Trial Description

Between 2010-2013, twelve healthy 30-59 year old volunteers (7 female, 5 male) with an acute recurrence of oral herpes infection (cold sores) were treated. Volunteers presented themselves when the onset of initial HSV symptoms (itching of the lips, burning or tingling near the lips or mouth area) occurred or had progressed to visible skin disorders on the outer lips. Observed skin disorders included small to large blisters filled with clear yellowish fluid or external herpetic lesions including leaking red blisters.

Oral herpes infection of the mouth area is mainly caused by the herpes simplex virus type 1 (HSV-1). However, sometimes HSV-2 is spread to the mouth during oral sex, causing oral herpes. The type of HSV infection (HSV-1 or HSV-2) was not analyzed.

The antibody was packaged as sterile solutions either in PBS or PBS/ash créme (1:1) at concentrations of 0.7-1 mg/ml. Participants applied approx. 10 µl of the antibody topically once, once per day for two days or for a total of three times maximum.

2. Results

ZOVIRAX Cream had been evaluated in 2 double-blind, randomized, placebo (vehicle)-controlled trials (see Zovirax N-. Zovirax Prescribing Information. http://wwwaccessdatafdagov/drugsatfda_docs/label/2002/21478_zovirax_Ib|pdf#page=1&zoom=auto,0,792).

In the Zovirax studies, subjects were instructed to initiate treatment within 1 hour of noticing signs or symptoms and continue treatment for 4 days, with application of study medication 5 times per day. In both studies, the mean duration of the recurrent herpes labialis episode was approximately one-half day shorter in the subjects treated with ZOVIRAX Cream (n=682) compared with subjects treated with placebo (n=703) (approximately 4.5 days versus 5 days, respectively). No significant difference was observed between subjects receiving ZOVIRAX Cream or vehicle in the prevention of progression of cold sore lesions.

Compared to previous HSV outbreaks that have been treated with aciclovir (Zovirax créme) all participants using the antibody solution reported a fast symptom and pain relief within 24 h after application of the antibody. In contrast to the experiences with aciclovir therapy active blisters regressed and did not turn into weeping blisters when treated topically with the antibody. When antibody treatment was started at the stage of visible external herpetic lesions, participants reported a rapid healing and disappearance of crusted areas. All participants reported in contrast to their experience with Zovirax that the infected area did not spread upon antibody treatment.

One volunteer experienced Herpes labialis at the upper and lower lip at the same time and started antibody treatment for the upper lip (three times) and Zovirax treatment for the lower lip (3-4 times a day for 3 days). At time of treatment several small blisters were visible. For the antibody treated HSV infection a quick recovery was observed. Blisters of the upper lip disappeared within 24 h, the swelling subsided within 48 h and no lesions occurred. The infection of lower lip treated with Zovirax remained painful for 3 days, blisters grew together into larger blister which eventually broke open. The occurred lesions took two weeks to heal.

Efficacy of the treatment seemed to be independent from the antibody formulation (PBS or PBS/ash créme).

Interestingly the participants have the impression that the overall rates of clinical reactivation tend to be reduced.

Example 2: Topical Application of Anti-HSV mAb hu2c in Animal Experiments

The ability of the humanized monoclonal antibody hu2c to alter the clinical course of acute genital HSV-2 infection in immunodeficient mice following a single topical treatment with 200 µg mAb hu2c (5 mg/ml) was investigated. To infect 100% of mice as assessed by visible lesions and culture of vaginal lavage, a viral inoculum of 5×105 PFU of HSV-2 G was delivered to the vagina of anesthetized mice.

Although acute HSV-1 or HSV-2 infections result in a fatal outcome in 100% of mice with severe combined immunodeficiency when compared to 70-90% mortality in immunocompetent mice, the immunodeficient model has nevertheless been chosen to discriminate a possible clinical efficacy of the therapy from an elimination of the viral infection due to immune effector cells of the mouse (Minagawa et al., Arch Virol 103, 73-82 (1988); Nagafuchi et al., J Gen Virol 44, 715-723 (1979)). Within genital mucosa the expansion rates of HSV-2 are extremely rapid. At 24 h after viral challenge infected mice received topically at the infected area either twice per day for 4 days 1 mg acyclovir (ACV) (25 mg/ml) or 40 µl buffer (PBS) or a single treatment of 200 µg mAb hu2c (5 mg/ml) or 200 µg control mAb (5 mg/ml). Clinical efficacy of the HSV-specific mAb was compared to the irrelevant mAb (isotypcontrol), ACV and PBS treatment by means of Kaplan-Meier survival curves and daily assessment of the clinical status of the mucous membranes of the genital and anal area. Results from mice displaying visible infection (perineal hair loss, reddening, swelling) and detectable peripheral replication 24 h after infection were evaluated.

As expected, no significant differences in overall survival were observed in control groups treated either with an irrelevant mAb vs PBS and all mice were dead by day 7 after infection (FIGS. 1A & B). Surprisingly, a single topical application of mAb hu2c to the outer genital infected epithelium resulted in a statistically significant difference in survival curves (P=0.003) when compared to the control groups (FIG. 1 A) and even prevented the lethal outcome of the infection in one mouse. Survival curves of the antibody hu2c treated group (FIG. 1 A) and the ACV treated group (FIG. 1 B) showed no significant differences (P>0.5) although ACV was applied twice daily for 4 days.

The medical advantage of the topical antibody therapy over the standard therapy with ACV became even more apparent when evaluating the clinical status of the acute genital infection over a period of 14 days (FIG. 2). A clinical score grading can be applied to investigate if the clinical course of an infection can be altered upon treatment (Minagawa et al., Arch Virol 103, 73-82 (1988); Sanna et al., Virology 215, 101-106 (1996)).

The clinical status of vaginitis/vulvitis was scored as follows: 0, lack of symptoms, no lesions; 1-2, redeness and/or swelling (erosion); 3, localized lesion <1 mm; 4-5, localized lesion 2-3 mm; 6-7 localized lesion 4-5 mm; 8-9, severe hyperemia, destruction of the epithelium and stroma with necrosis; 10, systemic signs, death.

Acute genital HSV-2 infection resolved in 7 out of 8 mice (88%) within 48 h post single topical treatment with anti-HSV mAb hu2c (FIG. 2D).

In contrast, animals treated with ACV displayed an extremely heterogeneous clinical grading. At 48 h under ongoing treatment with ACV (twice per day, for 4 days) local genital symptoms resolved only in 1 out of 8 mice (13%), and 72 h after commencement of ACV treatment only 5 out of 8 mice (63%) had no local signs (FIG. 2C). Although both, the hu2c antibody and ACV were applied only topically, HSV-2 lethal encephalitis could be prevented in 1 out of 8 mice in both cases.

Mice either treated with buffer or an irrelevant control mAb had progressive local HSV-2 infections spreading across the genital and anal areas and systemic dissemination of the virus resulted in the death of all animals at day 7 (FIGS. 2 A & B).

The invention claimed is:

1. A method of treating an acute infection of mucosal or epidermal tissue in a subject caused by HSV-1 or HSV-2, wherein the method comprises administering to the subject a neutralizing full-length anti-HSV antibody, wherein the subject is suffering from an acute infection of one or more of Herpes simplex labialis, Herpes simplex genitalis, chronic or disseminated cutaneous herpes simplex infection, Herpes gladiatorum or Eczema herpeticum, wherein the antibody comprises complementarity determining regions $V_H$CDR1 comprising SEQ ID NO: 1, $V_H$CDR2 comprising SEQ ID NO: 2, $V_H$CDR3 comprising SEQ ID NO: 3, $V_L$CDR1 comprising SEQ ID NO: 4, $V_L$CDR2 comprising SEQ ID NO: 5, and $V_L$CDR3 comprising SEQ ID NO:6, wherein said antibody inhibits cell-to-cell spread, and wherein said antibody is topically administered to mucosal or epidermal tissue.

2. The method of claim 1, wherein said anti-HSV antibody is a monoclonal or a polyclonal antibody.

3. The method of claim 1, wherein said anti-HSV antibody is a humanized or fully human antibody.

4. The method of claim 1, wherein said anti-HSV antibody recognizes the glycoprotein B (gB) of the HSV-1 and/or HSV-2.

5. The method of claim 1, wherein the antibody is capable of inhibiting cell-to-cell spread independent from antibody-dependent cellular cytotoxicity (ADCC) and/or complement-dependent cytotoxicity (CDC).

6. The method of claim 1, wherein the antibody is capable of inhibiting the spreading of HSV from an infected cell to an adjacent second non-infected cell (cell to cell spread).

7. The method of claim 1, wherein the antibody comprises an amino acid sequence with at least 70% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

8. The method of claim 1, wherein said antibody comprises the VH of SEQ ID NO:9 and the VL of SEQ ID NO:10.

9. The method of claim 1, wherein said antibody recognizes the same epitope as mAb 2c, wherein said epitope is located at the amino acids 172-195 and 295-313 of glycoprotein B of HSV-1 and HSV-2.

10. The method of claim 1, wherein said antibody is the mAb 2c antibody.

11. The method of claim 1, wherein said antibody is to be topically applied to infected mucosal or epidermal tissue of the lips, genitals, nose, ears, eyes, fingers, toes and/or skin areas throughout the body, preferably on the head, the jaw area, neck, chest, face, stomach and/or legs.

12. The method of claim 1, wherein said antibody is to be topically applied to areas surrounding the infected mucosal or epidermal tissue.

13. The method of claim 1, wherein said antibody is to be administered in combination with a virostatic agent.

14. The method of claim 13, wherein said virostatic agent is selected from the group consisting of the drug classes of nucleoside analogues, pyrophosphate analogues, nucleotide analogues, an amantadin derivative, and helicase-primase inhibitors.

15. The method of claim 14,
wherein said nucleoside analogue is selected from the group consisting of Acyclovir, Penciclovir, Valacyclovir and Famaciclovir;
wherein said pyrophosphate analogue is Foscarnet;
wherein said nucleotide analogue is Cidofovir;
wherein said amantadin derivative is Tromantandin; and
wherein said helicase-primase inhibitor is Pritelevir.

16. The method of claim 1, wherein the antibody is part of a pharmaceutical composition comprising at least one pharmaceutically acceptable excipient.

17. The method of claim 1, wherein said anti-HSV antibody comprises SEQ ID NO:9.

18. The method of claim 1, wherein said anti-HSV antibody comprises SEQ ID NO:10.

19. The method of claim 1, wherein symptoms of said acute infection include itching of the lips, burning or tingling near the lips or mouth area, or blisters.

\* \* \* \* \*